(12) United States Patent
Sandhu et al.

(10) Patent No.: US 9,216,070 B2
(45) Date of Patent: Dec. 22, 2015

(54) INTUITIVE USER GUIDED CONFIGURATION ROUTINE

(75) Inventors: Kulbir S. Sandhu, Fremont, CA (US); Venkata Adusumilli, Santa Clara, CA (US); Devanshi Shah, Santa Clara, CA (US); Jimmy Quoc Hy Duong, Millbrae, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 376 days.

(21) Appl. No.: 12/982,982

(22) Filed: Dec. 31, 2010

(65) Prior Publication Data

US 2012/0172795 A1    Jul. 5, 2012

(51) Int. Cl.
*G01L 1/00* (2006.01)
*G01D 18/00* (2006.01)
*G06F 19/00* (2011.01)
*A61B 19/00* (2006.01)

(52) U.S. Cl.
CPC ............ *A61B 19/56* (2013.01); *G06F 19/3406* (2013.01); *A61B 19/22* (2013.01); *A61B 19/5244* (2013.01)

(58) Field of Classification Search
CPC ..... G01N 21/27; G06F 19/3406; G06F 19/22; G06F 19/5244; G06F 9/56
USPC ........... 702/85, 42; 710/61; 604/95.01, 95.04; 600/424; 340/407.01
See application file for complete search history.

(56) References Cited

U.S. PATENT DOCUMENTS

| | | | |
|---|---|---|---|
| 6,233,476 B1 | 5/2001 | Strommer et al. | |
| 6,690,963 B2 | 2/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,536,218 B2 | 5/2009 | Govari et al. | |
| 7,848,789 B2 | 12/2010 | Govari et al. | |
| 8,601,185 B2 * | 12/2013 | Sandhu et al. | ............. 710/61 |
| 2004/0068173 A1 | 4/2004 | Viswanathan | |
| 2006/0041178 A1 | 2/2006 | Viswanathan | |
| 2006/0058647 A1 | 3/2006 | Strommer | |
| 2006/0281990 A1 | 12/2006 | Viswanathan | |
| 2007/0016068 A1 * | 1/2007 | Grunwald et al. | ............ 600/468 |
| 2008/0033284 A1 | 2/2008 | Hauck | |
| 2008/0249536 A1 | 10/2008 | Stahler et al. | |
| 2009/0005675 A1 * | 1/2009 | Grunwald et al. | ............ 600/424 |
| 2009/0012533 A1 | 1/2009 | Barbagli et al. | |
| 2009/0247942 A1 | 10/2009 | Kirschenman | |
| 2009/0247943 A1 | 10/2009 | Kirschenman et al. | |
| 2009/0247944 A1 | 10/2009 | Kirschenman et al. | |
| 2009/0247993 A1 | 10/2009 | Kirschenman | |
| 2009/0248042 A1 | 10/2009 | Kirschenman et al. | |
| 2010/0073150 A1 * | 3/2010 | Olson et al. | ................ 340/407.1 |
| 2010/0256558 A1 * | 10/2010 | Olson et al. | ................ 604/95.01 |
| 2011/0015569 A1 | 1/2011 | Kirschenman et al. | |
| 2011/0144657 A1 * | 6/2011 | Fish et al. | ..................... 606/130 |

FOREIGN PATENT DOCUMENTS

WO    WO2009120982    10/2009

* cited by examiner

*Primary Examiner* — John H Le
(74) *Attorney, Agent, or Firm* — Dykema Gossett PLLC

(57) ABSTRACT

A user-guided configuration routine for use with a remote catheter guidance system configured to calibrate of one or more medical devices of the remote catheter guidance system with minimal user input. The user-guided configuration routine being configured to determine the appropriate configuration steps from diagnostic data received from the remote catheter guidance system or from a user.

18 Claims, 16 Drawing Sheets

INTUITIVE USER GUIDED CONFIGURATION ROUTINE

BACKGROUND OF THE INVENTION a. Field of the Invention

This disclosure relates to a remote catheter guidance system. More particularly, this disclosure relates to a graphical user interface for controlling a remote catheter guidance system, and a user-guided configuration routine for automatically configuring a remote catheter guidance system.

b. Background Art

Electrophysiology (EP) catheters are used in a variety of diagnostic and therapeutic medical procedures. For example, EP catheters can be used to correct conditions such as atrial arrhythmia, including ectopic atrial tachycardia, atrial fibrillation, and atrial flutter. Atrial arrhythmia can create a variety of dangerous conditions including irregular heart rates, loss of synchronous atrioventricular contractions, and statis of blood flow, which can lead to a variety of ailments or death.

EP catheters typically have one or more electrodes mounted thereon for use in the performance of mapping, ablation, and/or other diagnostic or therapeutic procedures. In an instance wherein the catheter is configured for use in an ablation procedure, electrodes mounted on or in the catheter are used to create tissue necrosis (i.e., lesions) in cardiac tissue to correct conditions such as those identified above. It is believed that the primary cause of atrial arrhythmia is stray electrical signals within the left or right atrium of the heart. Accordingly, by applying ablative energy (e.g., radio frequency energy, cryoablation, lasers, chemicals, high-intensity focused ultrasound, etc.) to the tissue, lesion(s) are formed therein that disrupt undesirable electrical pathways, thereby preventing or at least substantially limiting, the stray electrical signals that can lead to arrhythmias.

In order to perform procedures such as those described above, the catheter must be inserted into the patient's body and maneuvered through the vasculature to a desired anatomical structure or site (e.g., the heart). One way this can be done is with the use of a medical device known as a sheath or catheter-introducer in conjunction with the catheter. Sheaths have a central lumen adapted to receive medical devices, such as, for example, catheters, and allow for the movement of the catheter therein. Sheaths also provide a measure of protection of the catheter tip while the catheter and sheath are being maneuvered into and through the vasculature. Once at the desired structure or site, the distal portion of the catheter containing one or more electrodes can be extended beyond the distal end of the sheath to allow for the performance of one or more procedures.

The catheter and/or sheath can contain one or more steering wires that run the length of the respective devices from the proximal end thereof to a point at or near the distal end thereof. These steering wires can be coupled at the proximal end thereof with an actuator. The combination of the steering wires and the manipulation of the actuator allow a physician to effect movement (i.e., deflection) of the distal end of the catheter and/or sheath in one or more directions, thus allowing the device to be navigated.

Considerable skill is required to accurately navigate the catheter and sheath within the patient's vasculature and anatomical structures, such as, for example, the heart, and can be made considerably easier through the use of a remote catheter guidance system, such as, for example, a remote catheter guidance system.

Although remote catheter guidance systems provide precise control of catheter movements, such systems generally require a physician to manually navigate the catheter and any associated sheath through the patient vasculature prior to attaching the catheter to the remote catheter guidance system. When attaching the catheter the physician must manually configure the remote catheter guidance system by performing a series of calibration steps required for the guidance system to accurately maneuver the catheter. Should the physician perform the steps in the wrong order or omit a step, the guidance system can require the calibration process be repeated. The calibration process also becomes necessary when the catheter or an attached sheath malfunctions and must be replaced, or when the guidance system is recovering from a system failure such as a loss of power. Manual configuration in these situations can take ten minutes or more and unduly increases the length of procedures and the attendant risks to the patient. An example of a method for calibrating a remote device can be seen generally by reference to U.S. application Ser. No. 11/843,589, filed 22 Aug. 2007, owned by the common assignee of the present disclosure, and hereby incorporated by reference in its entirety.

Automated catheter guidance systems can utilize visualization, navigation, and/or mapping systems to determine the location or position and orientation of the catheter within the patient's heart. Various types of visualization, navigation, and mapping systems can be used, such as, for example, electric field-based systems, magnetic field-based systems, and hybrid systems combining both electrical and magnetic fields. Among other things, these systems generate a model of one or more anatomical structures that are used as the primary navigational reference for the remote catheter guidance system.

Although remote catheter guidance systems can be used in conjunction with a visualization, navigation, and mapping system, the operation is hindered by the fact that both the visualization, navigation, and mapping system and the remote catheter guidance system maintain independent controls. Thus, the physician must switch between the individual controls of each system to utilize both. Such switching is problematic in that it not only unduly complicates clinical procedures but also creates an inherent delay between perceiving a catheter movement within the visualization, navigation, and altering or stopping the movement using the remote catheter guidance system controls.

Accordingly, the inventors herein have recognized a need for improved control of remote catheter guidance systems, as well as improved ways of configuring such systems that will minimize and/or eliminate one or more of the deficiencies in conventional remote catheter guidance systems.

BRIEF SUMMARY OF THE INVENTION

It is desirable to be able to provide an intuitive graphical user interface for controlling a remote catheter guidance system and a visualization, navigation, and mapping system by generating a user interface window configured to receive user input directed to the control of the remote catheter guidance system or the visualization, navigation, and mapping system. The user interface window can further be configured to receive input directing the position of graphical user interfaces within the interface window.

The user interface is configured to receive user input directing the remote catheter guidance system to deflect, translate, or rotate a medical device of the system. The user interface also displays graphical displays representing diagnostic data of the remote catheter guidance system, or the diagnostic data itself.

It is further desirable for the user interface to allow a user to launch a user-guided configuration routine for configuring one or more medical devices of the system. The user-guided configuration routine generates a desired graphical user interface displayed within the user interface window. The user-guided configuration routine also allows the display of desired information to the user and the ability to receive user input commands. The configuration routine can include one or more configuration steps executed to calibrate one or more medical device of the system.

The foregoing and other aspects, features, details, utilities, and advantages of the present invention will be apparent from reading the following description and claims, and from reviewing the accompanying drawings.

DETAILED DESCRIPTION OF THE INVENTION

Before proceeding to a detailed description of a graphical user interface system for use in the operation and control of a remote control and guidance system for one or more medical devices, and a user-guided configuration routine for such a system, a brief overview (for context) of an exemplary remote catheter guidance system (RCGS) will first be described. It will be appreciated, however, that the description below of one or both of the graphical user interface system and user-guided configuration routines can find application in remote control and guidance systems other than remotely guided catheter-based systems. For example an RCGS can be driven by linear and/or rotary actuators. In an alternative embodiment, the RCGS can comprise a magnetic-based control and guidance system. Accordingly, those of ordinary skill in the art will appreciate that the present disclosure is not limited to any one type of RCGS, and that systems other than remotely guided catheter-based systems remain within the spirit and scope of present disclosure.

Accordingly, the description below of the RCGS details how several linearly driven electric motors can be used to control the translation, distal bending and virtual rotation of two medical devices, namely, a catheter and a surrounding sheath. After the description of the RCGS, the present specification describes a graphical user interface system and user-guided configuration routine for use in the operation, control, and/or configuration of the RCGS.

Figure 1:
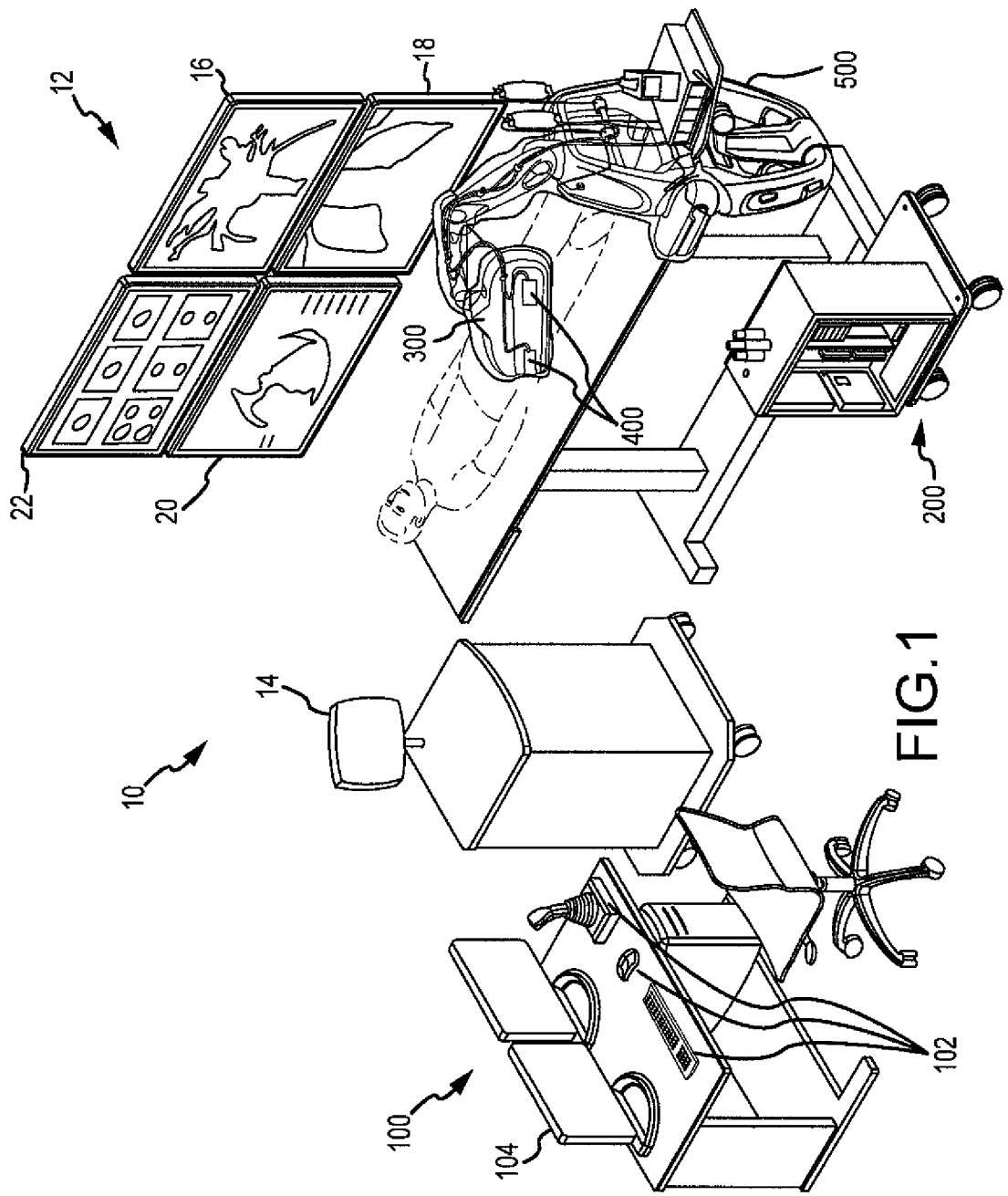
FIG. 1 is an isometric diagrammatic view of a remotely based catheter system, illustrating an exemplary layout of various system components.

In this regard, and now referring to the drawings wherein like reference numerals are used to identify identical components in the various views, FIG. 1 is a diagrammatic view of an exemplary RCGS 10 in which several aspects of a graphical user interface and user-guided configuration routine can be used.

Exemplary RCGS System Description.

RCGS 10 can be likened to power steering for a medical device system. The RCGS 10 can be used, for example, to manipulate the location and orientation of medical devices, such as, for example, catheters and sheaths, in a heart chamber or in another body organ, cavity, or lumen. For purposes of illustration and clarity only, the description below will be limited to an embodiment wherein the medical devices manipulated by the RCGS 10 are catheters and/or sheaths. It will be appreciated, however, that the RCGS 10 can be configured to manipulate medical devices other than catheters and sheaths, and therefore, these medical devices remain within the spirit and scope of the present disclosure. The RCGS 10 thus provides the user with a similar type of control provided by a conventional manually-operated system, but allows for repeatable, precise, and dynamic movements. For example, a user such as an electrophysiologist, can identify locations (potentially forming a path) on a rendered computer model of the cardiac anatomy. The system can be configured to relate those digitally selected points to positions within a patient's actual/physical anatomy, and can thereafter command and control the movement of the catheter and/or sheath to the defined positions. Once at the specified target position, either the user or the system can perform the desired diagnostic or therapeutic function, such as, for exemplary purposes only, an ablation procedure. The RCGS 10 enables full remote navigation/guidance and control.

As shown in FIG. 1, the RCGS 10 can generally include one or more monitors or displays 12, a visualization, mapping and navigation (including localization) system 14, a human input device and control system (referred to as "input control system") 100, an electronic control system 200, a manipulator assembly 300 for operating a device cartridge 400, and a manipulator support structure 500 for positioning the manipulator assembly 300 in proximity to a patient or a patient's bed.

Displays 12 are configured to visually present to a user information regarding patient anatomy, medical device location, or the like, originating from a variety of different sources. Displays 12 can include (1) an ENSITE VELOCITY monitor 16 (coupled to system 14—described more fully below) for displaying cardiac chamber geometries or models, displaying activation timing and voltage data to identify arrhythmias, and for facilitating guidance of catheter movement; (2) a fluoroscopy monitor 18 for displaying a real-time x-ray image or for assisting a physician with catheter movement; (3) an intra-cardiac echo (ICE) display 20 to provide further imaging; and (4) a display 22.

The system 14 is electrically coupled to (i.e., via wires or wirelessly) to the electric control system 200, and is configured to provide many advanced features, such as visualization, navigation, and mapping support and positioning (i.e., determine a position and orientation (P&O)) of a sensor-equipped medical device, for example, a P&O of a distal tip portion of a catheter. Such functionality can be provided as part of a larger visualization, navigation, and mapping system, for example, an ENSITE VELOCITY system running a version of NavX software commercially available from St. Jude Medical, Inc, of St. Paul, Minn., and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present disclosure, and hereby incorporated by reference in its entirety. The system 14 can comprise conventional apparatus known generally in the art, for example, the ENSITE VELOCITY system described above or other known technologies for locating/navigating a catheter in space (and for visualization), including for example, the CARTO visualization and location system of Biosense Webster, Inc., (e.g., as exemplified by U.S. Pat. No. 6,690,963 entitled "System for Determining the Location and Orientation of an Invasive Medical Instrument" hereby incorporated by reference in its entirety), the AURORA® system of Northern Digital Inc., a magnetic field based localization system such as the gMPS system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3 visualization and location system of Biosense Webster, Inc. (e.g., as exemplified by U.S. Pat. Nos. 7,536,218, and 7,848,789 both of which are hereby incorporated by reference in its entirety). Some of the localization, navigation and/or visualization systems can involve providing a sensor for producing signals indicative of catheter location and/or orientation information, and can include, for example one or more electrodes in the case of an impedance-based localization system such as the ENSITE VELOCITY system running NavX software, which electrodes can already exist in some instances, or alternatively, one or more coils (i.e., wire windings) configured to detect one or more characteristics of a low-strength magnetic field, for example, in the case of a magnetic-field based localization system such as the gMPS system using technology from MediGuide Ltd. described above.

The input control system 100 is electrically coupled (i.e., via wires or wirelessly) to the electronic control system 200 and is configured to allow a user, such as an electrophysiologist, to interact with the RCGS 10, in order to control the movement and advancement/withdrawal of one or both of a catheter and sheath (see, e.g., commonly assigned U.S. patent application Ser. No. 12/751,843 filed Mar. 31, 2010 entitled "ROBOTIC CATHETER SYSTEM" and PCT/US2009/038597 entitled "ROBOTIC CATHETER SYSTEM WITH DYNAMIC RESPONSE", published as WO 2009/120982; the entire disclosure of both applications being hereby incorporated by reference). The input control system can comprise one or more user input devices 102 and a display device 104. Generally, numerous types of user input devices 102 and related controls can be employed, including, without limitation, instrumented traditional catheter handle controls, oversized catheter models, instrumented user-wearable gloves, touch screen display monitors, 2-D input devices, 3-D input devices, spatially detected styluses, keyboards, computer mice, joysticks, joyrods, microphones, and the like. For a further description of exemplary input apparatus and related controls, see, for example, commonly assigned U.S. patent application Ser. No. 12/933,063 entitled "ROBOTIC CATHETER SYSTEM INPUT DEVICE" and U.S. patent application Ser. No. 12/347,442 entitled "MODEL CATHETER INPUT DEVICE", the entire disclosure of both applications being hereby incorporated by reference. The user input devices 102 can be configured, for example, to manipulate a target or cursor on an associated display, such as, for example, the display device 104. The display device 104 can comprise one of any number of display devices known in the art, such as, for example, computer monitors, LCD displays, CRT displays, and the like. As will be described in greater detail below, the input control system 100 can be configured to display, and allow a user of the RCGS 10 to interact with, a graphical user interface or user interface window that can be used in the control and operation of the RCGS 10. As will be described below, the graphical user interface and user interface window include a plurality of user-selectable or inputtable fields (e.g., buttons, sliders, selectable menus, etc.). In each instance, the user can interact with the fields using the user input devices 102 of the input control system 100.

The electronic control system 200 is configured to translate (i.e., interpret) inputs (e.g., motions, instructions, voice commands, etc.) of the user at an input device, such as, for example, the user input device 102 of the input control system 100, or from another source into a resulting movement of the catheter and/or surrounding sheath. In this regard, the system 200 includes a programmed electronic control unit (ECU) in communication with a memory or other computer readable media (memory) suitable for information storage. Relevant to the present disclosure, the electronic control system 200 is configured, among other things, to issue commands (i.e., actuation control signals) to the manipulator assembly 300 (i.e., to the actuation units thereof—electric motors) to move or bend the catheter and/or sheath to prescribed positions and/or in prescribed ways, all in accordance with the received user input and a predetermined operating strategy programmed into the system 200. In addition to the instant description, further details of a programmed electronic control system can be found in commonly assigned U.S. patent application Ser. No. 12/751,843 filed Mar. 31, 2010 entitled "ROBOTIC CATHETER SYSTEM" described above.

It should be understood that although the visualization, navigation, and mapping system 14 and the electronic control system 200 are shown separately, integration of one or more computing functions can result in a system including an ECU on which can be run both (i) various control and diagnostic logic pertaining to the RCGS 10 and (ii) the visualization, navigation, and mapping functionality of system 14. For purposes of clarity and illustration only, the description below will be limited to an embodiment wherein the ECU is configured to perform the various control and diagnostic functionality of the RCGS 10 as well as the functionality of the visualization, navigation, and mapping system 14. It will be appreciated, however, that in other exemplary embodiments, the system 14 and the electronic control system 200 can have separate and distinct ECUs that are electrically coupled and configured for communication with each other. This arrangement remains within the spirit and scope of the present disclosure.

The manipulator assembly 300, in response to such commands, is configured to maneuver the medical device (e.g., translation movement, such as advancement and withdrawal of the catheter and/or sheath), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations, as detailed below) for linearly actuating one or more control members (e.g., steering wires) associated with the medical device for achieving the above-described translation, deflection and/or rotation (or virtual rotation). In addition to the description set forth herein, further details of a manipulator assembly be can be found in commonly assigned U.S. patent application Ser. No. 12/347,826 titled "ROBOTIC CATHETER MANIPULATOR ASSEMBLY", the entire disclosure of which is hereby incorporated by reference.

A device cartridge 400 is provided for each medical device controlled by the RCGS 10. For this exemplary description of an RCGS 10, one cartridge is associated with a catheter and a second cartridge is associated with an outer sheath. The cartridge is then coupled, generally speaking, to the RCGS 10 for subsequent remotely-controlled movement. In addition to the description set forth herein, further details of a device cartridge can be found in commonly owned U.S. patent application Ser. No. 12/347,835 entitled "ROBOTIC CATHETER DEVICE CARTRIDGE" and U.S. patent application Ser. No. 12/347,842 "ROBOTIC CATHETER ROTATABLE DEVICE CARTRIDGE", the entire disclosure of both applications being hereby incorporated by reference.

Figure 2:
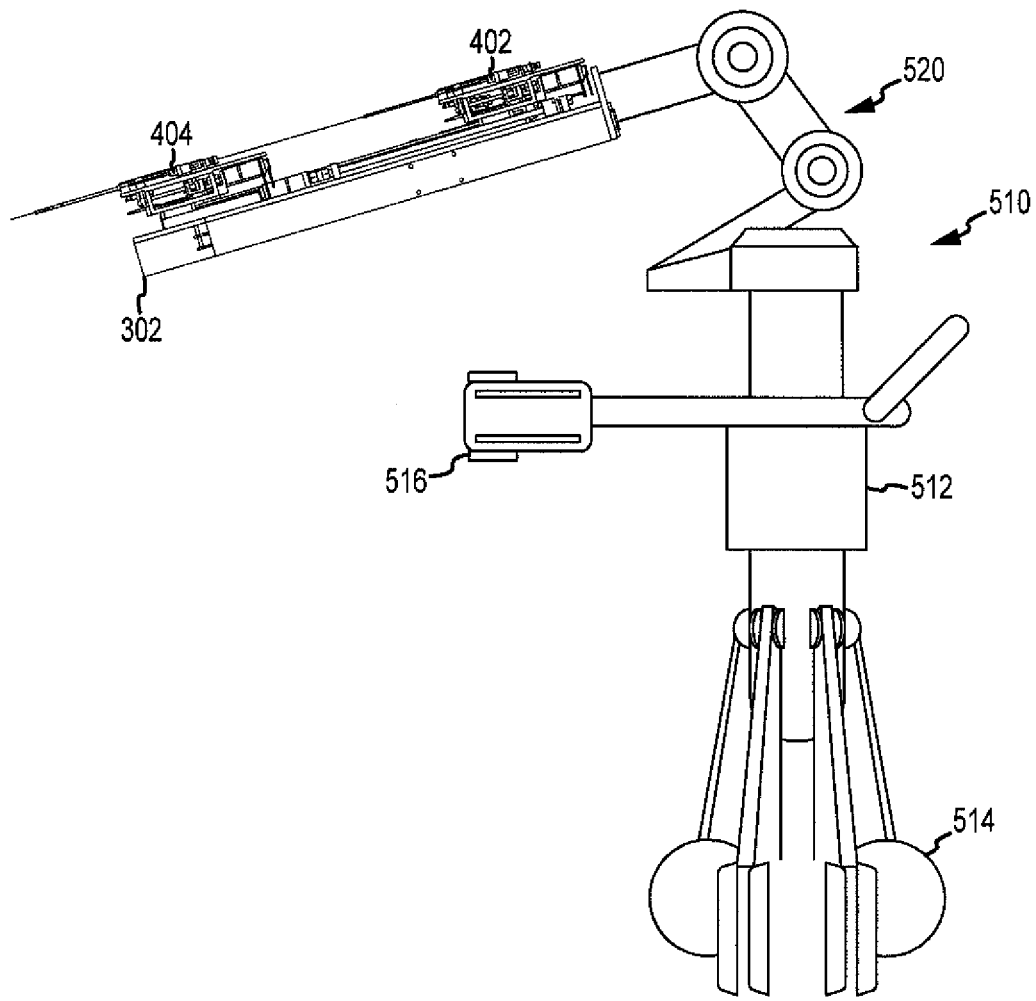
FIG. 2 is a side view of a manipulator assembly shown in FIG. 1, coupled to a remotely based catheter support structure, showing side views of catheter and sheath manipulation mechanisms.

FIG. 2 is a side view of an exemplary remotely based catheter support structure, designated structure 510 (see commonly owned U.S. patent application Ser. No. 12/347,811 entitled "ROBOTIC CATHETER SYSTEM" described above). The structure 510 can generally include a support frame 512 including retractable wheels 514 and attachment assembly 516 for attachment to an operating bed (not shown). A plurality of support linkages 520 can be provided for accurately positioning one or more manipulator assemblies, such as manipulator assembly 302. The assembly 302 is configured to serve as the interface for the mechanical control of the movements or actions of one or more device cartridges, such as catheter and sheath cartridges 402, 404 described below. Each device cartridge is configured to receive and retain a respective proximal end of an associated medical device (e.g., catheter or sheath). The assembly 302 also includes a plurality of manipulation bases onto which the device cartridges are mounted. After mounting, the manipulator assembly 302, through the manipulation bases, is capable of manipulating the attached catheter and sheath.

Figure 3A:
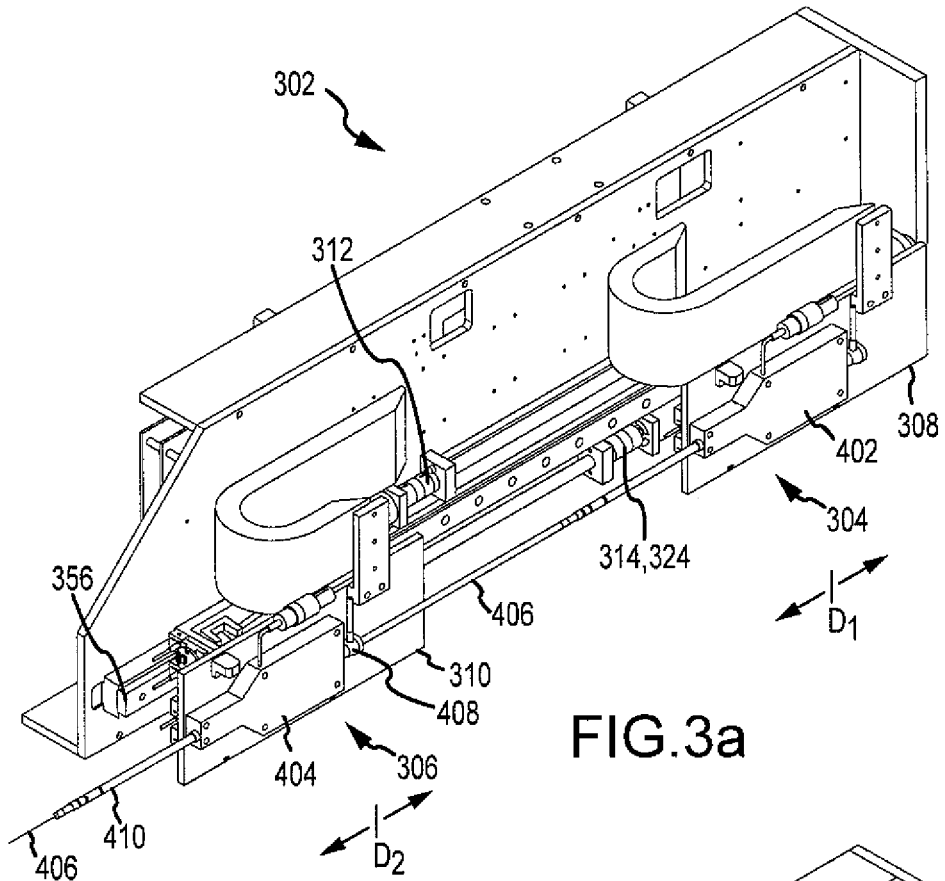
FIGS. 3a-3b are isometric views of a manipulator assembly shown in FIG. 2, showing the catheter and sheath manipulation mechanism in greater detail.
Figure 3B:
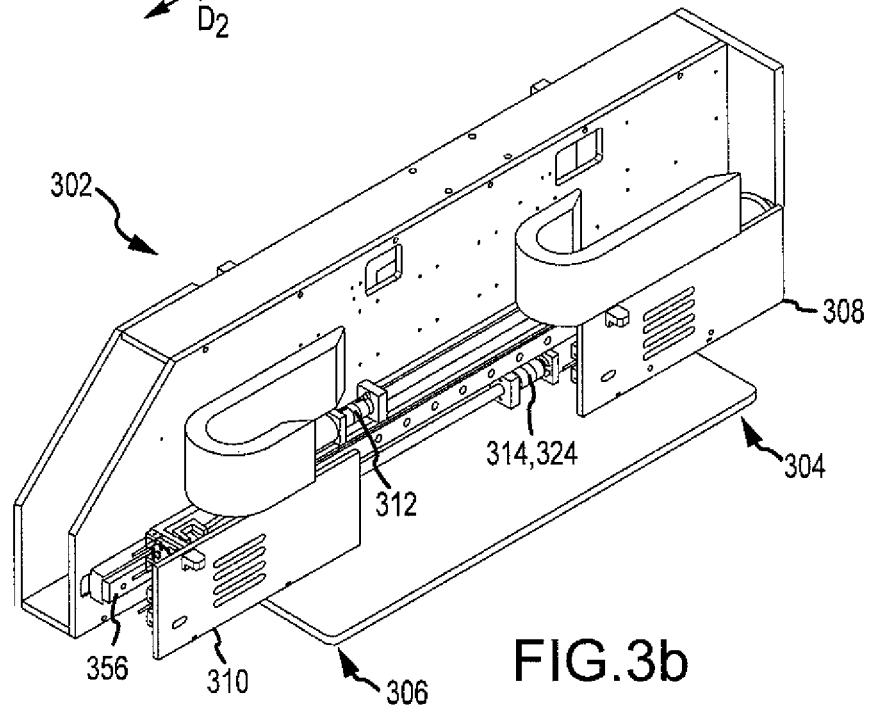
Figure 4A:
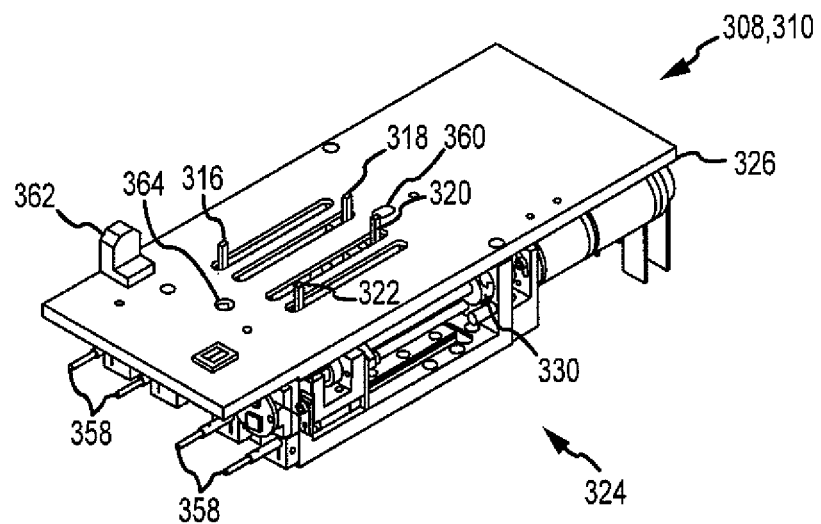
FIGS. 4a-4c are isometric views showing a sheath manipulation base of FIGS. 3a-3b in greater detail.
Figure 4B:
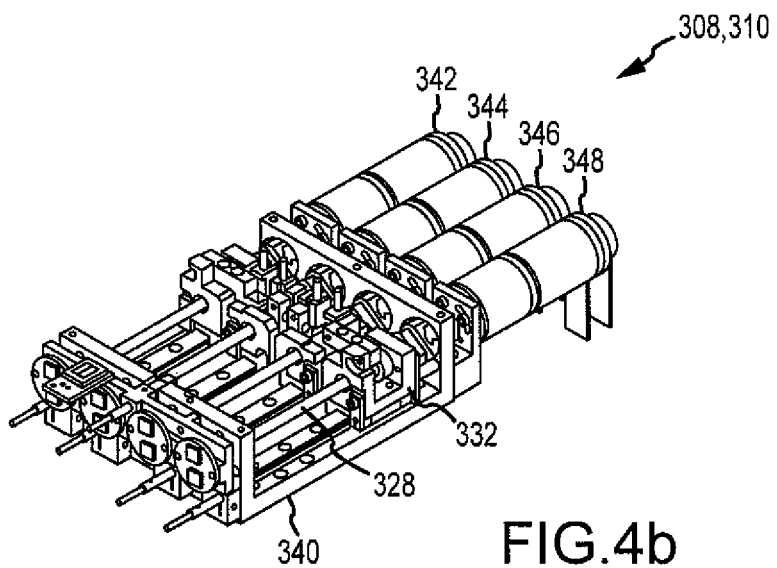
Figure 4C:
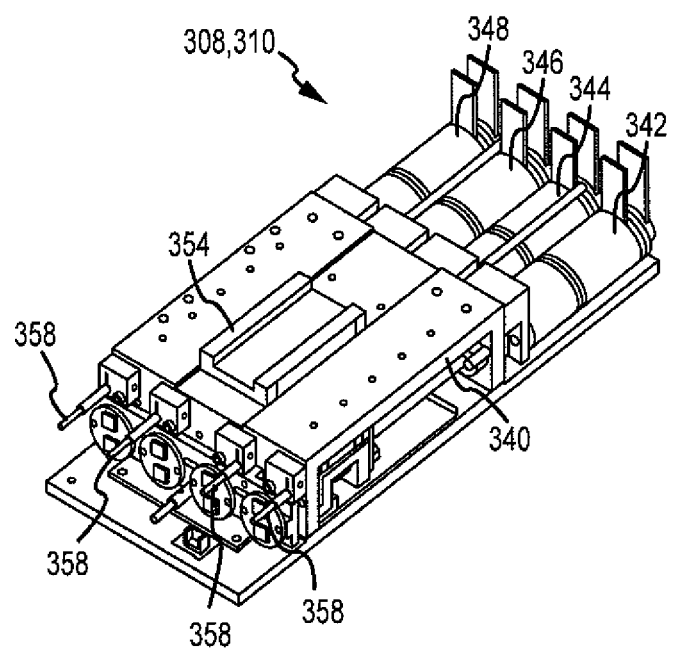
Figure 5A:
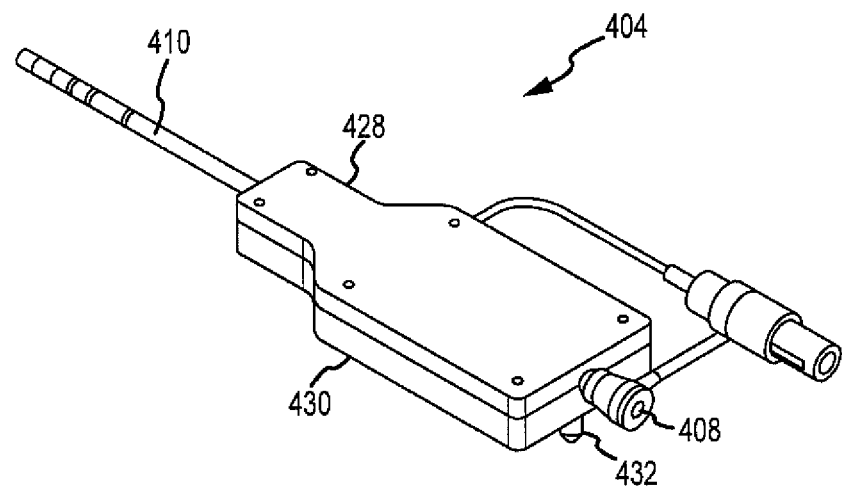
FIGS. 5a-5b are isometric views showing a sheath cartridge of FIGS. 3a-3b in greater detail.
Figure 5B:
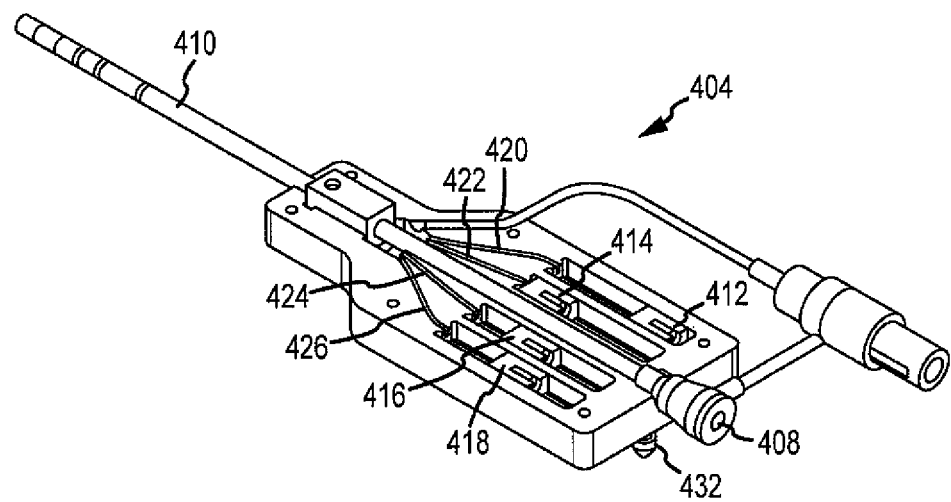

In the Figures to follow, FIGS. 3a-3b will show a manipulator assembly, FIGS. 4a-4c will show a manipulation base, and FIGS. 5a-5b will show a device cartridge.

FIG. 3a is an isometric view, with portions omitted for clarity, of manipulator assembly 302. Assembly 302 includes a catheter manipulator mechanism 304, a sheath manipulator mechanism 306, a catheter manipulation base 308, a sheath manipulation base 310, a first (catheter) drive mechanism 312, a second (sheath) drive mechanism 314, and a track 356. As further shown, assembly 302 further includes a catheter cartridge 402 and a sheath cartridge 404, with a catheter 406 having a proximal end opening 408 coupled to the catheter cartridge 402 and a sheath 410 coupled to the sheath cartridge 404.

Catheter and sheath manipulator mechanisms 304, 306 are configured to manipulate the several different movements of the catheter 406 and the sheath 410. First, each mechanism 304, 306 is configured to impart translation movement to the catheter 406 and the sheath 410. Translation movement here refers to the independent advancement and retraction (withdrawal) as shown generally in the directions designated D1 and D2 in FIG. 3a. Second, each mechanism 304, 306 is also configured to effect deflection of the distal end of either or both of the catheter and sheath 406, 410. Third, each mechanism 304, 306 can be operative to effect a so-called virtual (omni-directional) rotation of the distal end portion of the catheter 406 and the sheath 410. Virtual rotation, for example, can be made through the use of independent four-wire steering control for each device (e.g., eight total steering wires, comprising four sheath control wires and four catheter control wires). The distal end movement is referred to as "virtual" rotation because the outer surface of the sheath (or catheter) does not in fact rotate in the conventional sense (i.e., about a longitudinal axis) but rather achieves the same movements as conventional uni-planar deflection coupled with axial rotation. In addition to the present description of virtual rotation, further details can be found in PCT/US2009/038597 entitled "ROBOTIC CATHETER SYSTEM WITH DYNAMIC RESPONSE", published as WO 2009/120982.

Each manipulator mechanism 304, 306 further include a respective manipulation base 308, 310 onto which are received catheter and sheath cartridges 402, 404. Each interlocking base 308, 310 can travel in the longitudinal direction of the catheter/sheath (i.e., D1, D2 respectively) along a track 356. In an embodiment, D1 and D2 can each represent a translation of approximately 8 linear inches. Each interlocking base 308, 310 can be translated by respective high precision drive mechanisms 312, 314. Such drive mechanisms can include, for example and without limitation, an electric motor driven lead screw or ball screw.

The manipulator mechanisms 304, 306 are aligned with each other such that catheter 406 can pass through sheath 410 in a coaxial arrangement. Thus, sheath 410 can include a water-tight proximal sheath opening 408. Overall, the manipulator mechanisms 304, 306 are configured to allow not only coordinated movement but also relative movement between catheter and sheath cartridges 402, 404 (and thus relative movement between catheter and sheath).

FIG. 3b is an isometric view of manipulator assembly 302, substantially the same as FIG. 3a except that catheter and sheath cartridges 402, 404 are omitted (as well as catheter and sheath 406, 410) so as to reveal an exposed face of the manipulation bases 308, 310.

FIG. 4a is an isometric, enlarged view showing manipulation base 308 (and base 310) in greater detail. Each cartridge 402, 404 has an associated manipulation base 308, 310. Each base 308, 310 can include a plurality of fingers 316, 318, 320 and 322 (e.g., one per steering wire) that extend or protrude upwardly to contact and interact with steering wire slider blocks (i.e., such as slider blocks 412, 414, 416, 418 are best shown in FIG. 5b) to independently tension select steering wires 420, 422, 424, 426 (also best shown in FIG. 5b). Each finger can be configured to be independently actuated (i.e., moved back and forth within the oval slots depicted in FIG. 4a) by a respective precision drive mechanism, such as a motor driven ball screw 324. A plate 326 provides a surface onto which one of the cartridges 402, 404 are seated.

FIG. 4b is an isometric, enlarged view of base 308 (and base 310), substantially the same as FIG. 4a except with plate 326 omitted. Each motor-driven ball screw 324 (best shown in FIG. 4a) i.e., for both finger control and for cartridge translation control, can further include encoders to measure a relative and/or an absolute position of each element of the system. Moreover, each motor-driven ball screw 324 (i.e., for both finger control and cartridge translation control) can be outfitted with steering wire force sensors to measure a corresponding steering wire tension. For example, a corresponding finger 316, 318, 320 or 322 can be mounted adjacent to a strain gauge for measuring the corresponding steering wire tension. Each motor-driven ball screw 324 can include a number of components, for example only, a rotary electric motor (e.g., motors 342, 344, 346 and 348), a lead screw 328, a bearing 330 and a coupler 332 mounted relative to and engaging a frame 340. In the depicted embodiments linear actuation is primarily, if not exclusively, employed. However, some known examples of systems with rotary-based device drivers include U.S. application Ser. No. 12/150,110, filed 23 Apr. 2008 (the '110 application); and U.S. application Ser. No. 12/032,639, filed 15 Feb. 2008 (the '639 application). The '110 application and the '639 application are hereby incorporated by reference in their entirety as though fully set forth herein. These and other types of remote actuation can directly benefit from the teaching of the instant disclosure.

FIG. 4c is an isometric, enlarged view of base 308 (and base 310) that is taken from an opposite side as compared to FIGS. 4a-4b. Bases 308, 310 can include components such as a plurality of electrically-operated motors 342, 344, 346 and 348, respectively coupled to fingers 316, 318, 320 and 322. A bearing 354 can be provided to facilitate the sliding of bases 308, 310 on and along track 356. A plurality of inductive sensors (e.g. home sensors) 358 can also be provided for guiding each manipulation base to a home position.

FIG. 5a is an isometric, enlarged view showing, in greater detail, sheath cartridge 404. It should be understood that the description of sheath cartridge 404, except as otherwise stated, applies equally to catheter cartridge 402. Catheter 406 and sheath 410 can be substantially connected or affixed to respective cartridges 402, 404 (e.g., in the neck portion). Thus, advancement of cartridge 404 correspondingly advances the sheath 410 and retraction of cartridge 404 retracts the sheath 410. Likewise, although not shown, advancement of cartridge 402 correspondingly advances catheter 406 while a retraction of cartridge 402 retracts catheter 406. As shown, sheath cartridge 404 includes upper and lower cartridge sections 428, 430.

FIG. 5b is an isometric, enlarged view showing, in greater detail, sheath cartridge 404, with upper section 428 omitted to reveal interior components. Cartridge 404 can include slider blocks (e.g., as shown for cartridge 404, slider blocks 412, 414, 416, 418), each rigidly and independently coupled to a respective one of a plurality of steering wires (e.g., sheath steering wires 420, 422, 424, 426) in a manner that permits independent tensioning of each steering wire. Likewise, cartridge 402 for catheter 406 also includes slider blocks for coupling to a plurality (i.e., four) steering wires. Device cartridges 402, 404 can be provided as a disposable item that is capable of being easily positioned (e.g., snapped) into place (i.e., onto a respective base 408, 410). Sheath cartridge 404 can be designed in a similar manner as the catheter cartridge 402, but will typically be configured to provide for the passage of catheter 406.

In an alternative embodiment of the RCGS 10, the device cartridges 402, 404 can include a memory chip containing device data related to the type of catheter or sheath device attached to the device cartridge. The memory chip (e.g., an EEPROM chip) can be connected to the ECU by way of an electrical interface on the manipulation base 308, 310 allowing the ECU to access the device data. The memory chip can contain, for example, data indicating the make, model, serial number, physical dimensions, special features, and/or calibration data related to the catheter or sheath. In such an embodiment, a detection means can be present in the electrical interface of the manipulation base 308, 310 to initially detect the presence of a device cartridge 402, 404. The detection means can be an optical, magnetic, or electrical contact sensor configured to communicate an attachment signal to the ECU when a device cartridge 402, 404 is coupled to a base 308, 310, as described below. The ECU can energize the chip through the electrical interface and retrieve the device data for display in a graphical user interface or for use in device calibration, both of which are described in detail below.

Referring to FIGS. 4a and 5a, catheter and sheath cartridges 402, 404 are configured to be secured or locked down onto respective manipulation bases 308, 310. To couple cartridge 402 (and 404) with base 308 (and 310), one or more locking pins (e.g., 432 in FIG. 5a) on the cartridge can engage one or more mating recesses 360 in the base (see FIG. 4a). In an embodiment, such recesses 360 can include an interference lock such as a spring detent or other locking means. In an embodiment, such other locking means can include a physical interference that can require affirmative/positive action by the user to release the cartridge. Such action can include or require actuation of a release lever 362. Additionally, the cartridge can include one or more locator pins (not shown) configured to passively fit into mating holes on the base (e.g., 364 in FIG. 4a).

In operation, a user first manually positions catheter 406 and sheath 410 (with catheter 406 inserted in sheath 410) within the vasculature of a patient. Once the medical devices are roughly positioned in relation to the heart or other anatomical site of interest, the user can then engage or connect (e.g., "snap-in") the catheter and sheath cartridges 402, 404 into place on respective bases 308, 310. When a cartridge is interconnected with a base, the fingers fit into the recesses formed in the slider blocks. For example, with respect to the sheath cartridge 404 and sheath base 310, each of the plurality of fingers 316, 318, 320 or 322 fit into corresponding recesses formed between the distal edge of slider blocks 412, 414, 416, 418 and a lower portion of the cartridge housing (best shown in FIG. 5b). Each finger can be designed to be actuated in a proximal direction to respectively move each slider block, thereby placing the respective steering wire in tension (i.e., a "pull" wire). Translation, distal end bending and virtual rotation can be accomplished through the use of the RCGS 10.

Figure 6:
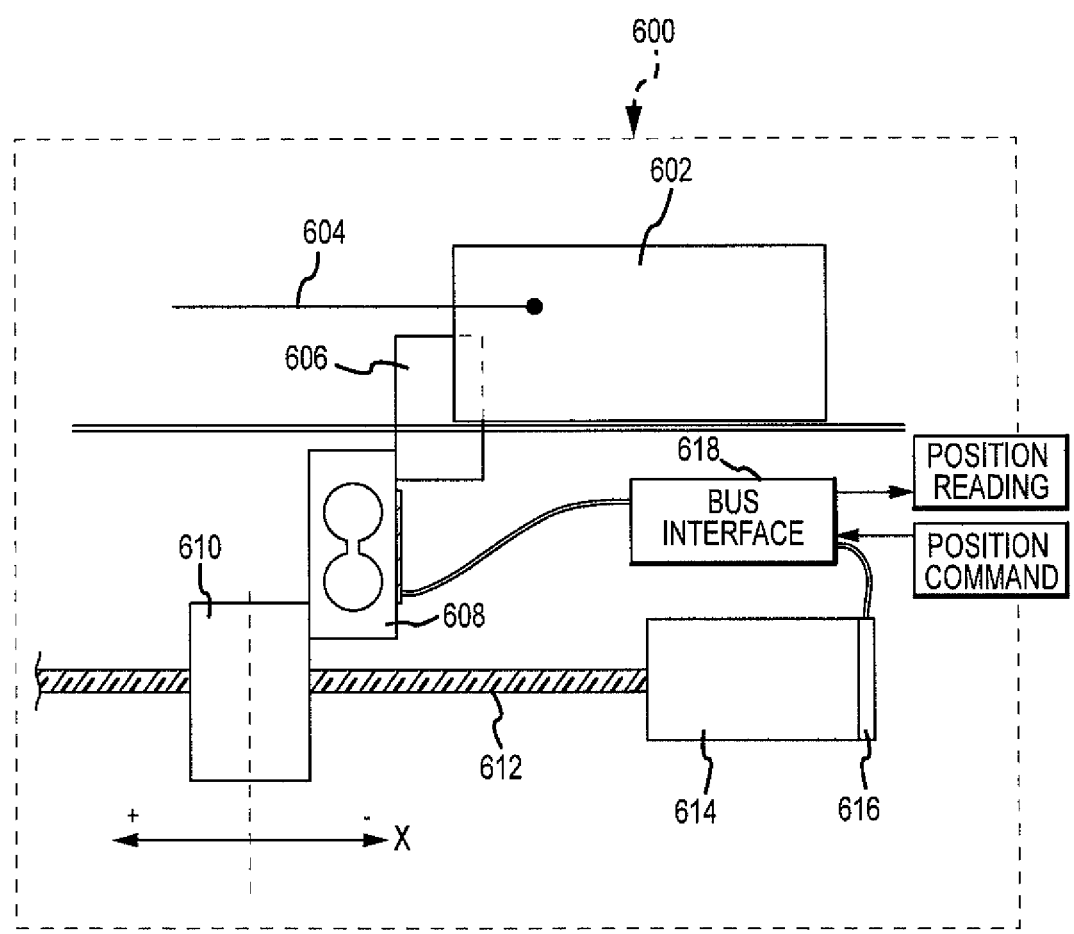
FIG. 6 is a diagrammatic view of the sheath manipulation mechanism of FIG. 2.

FIG. 6 is a diagrammatic view of a node suitable for connection to a communications bus (not shown) in RCGS 10. The node includes an actuation unit 600, similar to the actuation mechanisms described above (e.g., catheter actuation mechanism 304). The RCGS 10 can have at least ten such actuation units (i.e., one for each of the four catheter steering wires, four sheath steering wires, one catheter manipulation base and one sheath manipulation base), which as described include electric motors.

FIG. 6 shows in diagrammatic or block form many of the components described above—where appropriate, references to the earlier described components will be made. Actuation unit 600 includes a first, slidable control member 602 (i.e., slider as described above) that is connected to or coupled with a second, tensile control member 604 (i.e., steering wire as described above). The slider 602 can be configured to interface with a third, movable control member 606 (i.e., finger as described above). The finger 606 can further be operatively coupled with a portion of a sensor 608 (e.g., a force sensor), which, in turn, can be coupled with a translatable drive element 610 that can be mechanically moved. For example, without limitation, translatable drive element 610 can ride on or can otherwise be mechanically moved by a mechanical movement device 612 that, in turn, can be coupled with an electric motor 614. The mechanical movement device 612 can comprise a lead screw while the translatable drive element 610 can comprise a threaded nut, which can be controllably translated by screw 612 in the X+ or X− directions. In another embodiment, mechanical movement device 612 can include a ball screw, while translatable drive element 610 can include a ball assembly. Many variations are possible, as will be appreciated by one of ordinary skill in the art.

The actuation unit 600 also includes a rotary motor position encoder 616 that is coupled to the motor 614 and is configured to output a signal indicative of the position of the motor 614. The encoder 616 can comprise an internal, optical encoder assembly, integral with motor 614, configured to produce a relatively high accuracy output. The motor position sensor can operate in either absolute or relative coordinates. In an embodiment, a second motor position sensor (not shown) can also be provided, such as a potentiometer (or impedance-based), configured to provide a varying voltage output proportional to the motor's rotary position. The output of the secondary position sensor can be used as an integrity check of the operating performance of the primary position sensor (encoder) during start-up or initialization of the actuation unit.

Actuation unit 600 also includes one or more local controllers including a bus interface 618 to facilitate exchange of information between actuation unit 600 and electronic control system 200 (via the bus). The controller communicates with the main electronic control system 200 via the bus interface and bus and is configured, among other things, to (1) receive and execute motor actuation commands issued by the electronic control system 200 for controlling the movements of motor 614; and (2) receive and execute a command (issued by the electronic control system 200) to take a motor position sensor reading, for example, from encoder 616 and subsequently report the reading to system 200.

Graphical User Interface.

Figure 7:
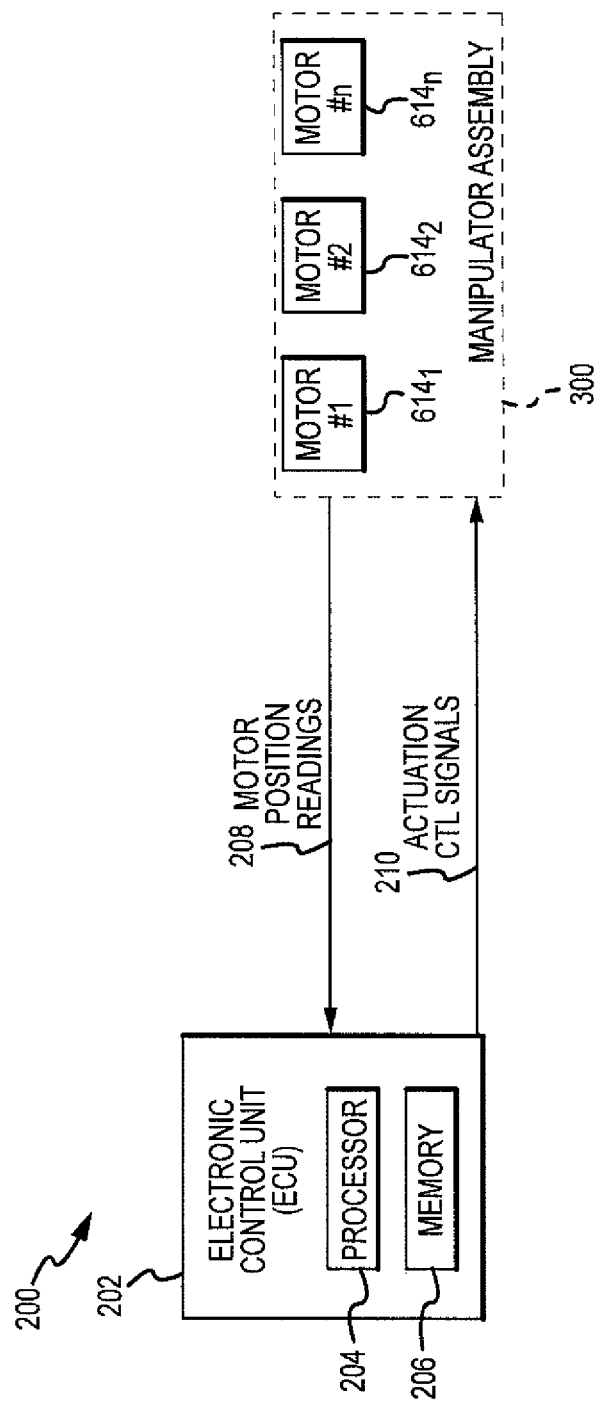
FIG. 7 is a block diagram of an apparatus for use in an remote control guidance system for controlling the precision drive motors of the medical device manipulator assembly.

FIG. 7 is a block diagram showing the electronic control system 200 of FIG. 1 in greater detail. The system 200 includes an ECU 202 having a processor 204 and an associated memory 206. The system 200 further includes logic, which in an embodiment can take the form of software stored in memory 206 and configured for execution by the processor 204, for performing at least the functionality described herein. The ECU 202 can comprise conventional apparatus known in the art. Generally, the ECU 202 is configured to perform core operating functions of the RCGS 10. Among other things, the ECU 202 is configured to generate graphical user interfaces, interpret user inputs, device location data, motor position readings 208 as well as other inputs and generate a plurality of actuation control signals 210, which are provided to the manipulator assembly 300. The actuation control signals 210 in turn are configured to control the plurality of actuation units 600, and therefore, the plurality of electric motors $614_1$, $614_2$, ..., $614_n$, so as to actuate a plurality of control members of the medical device (e.g., pull wires for deflection movement, manipulation bases for translation movement).

Figure 8:
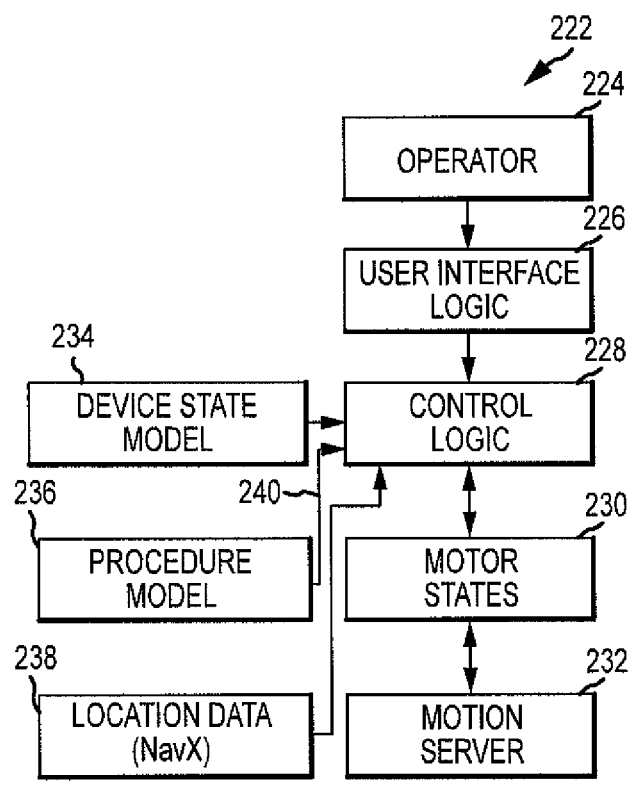
FIG. 8 is a block diagram showing, in greater detail, user interface logic and control logic used in the apparatus of FIG. 7.

FIG. 8 is block diagram of an apparatus 222 showing a functional configuration of the electronic control system 200. The apparatus 222 is configured for interaction with and by an operator/user 224. In many instances, the user 224 can refer, for example, to an electrophysiologist that is manipulating the catheter via the RCGS 10. The apparatus 222 includes user interface logic 226 and operating control logic 228, a motor state model 230, and a motion server 232.

The apparatus 222 receives inputs from the user 224 via user interface logic 226, which in turn interfaces with and receives user inputs from the input control system 100. The operator 224 can use one or more of the user input devices 102 of the input control system 100 to perform such tasks as, for example and without limitation, inputting desired catheter motions, rotating an anatomical model on a workstation display, and the like. The user input devices 102 can be further configured to allow the user 224 to provide inputs with respect to the anatomical model of a body portion of the patient (e.g., for setting up a pre-planned path for the catheter (i.e., setting way points), for initiating and conducting diagnostic and therapeutic procedures, etc.). The user interface logic 226 also displays information regarding the currently displayed (rendered) scene (e.g., the view angle, the mouse location, the catheter tip location, etc.). As will be described in greater detail below, in an exemplary embodiment, the user interface logic 226 is configured to generate a graphical user interface, or user interface window, that can be used to control, operate, and/or configure the RCGS 10.

The operating control logic 228 is configured to process incoming data from a plurality of sources, including the user interface logic 226 (as described above), the location data source 238 (i.e., the visualization, navigation, and mapping system 14, for example), as well as the diagnostic data contained in the motor state model 230 (e.g., to obtain the current motor states), and the device state model 234. The operating control logic 228 can further be configured to generate a procedure model 236 containing a record of the data processed by the control logic during a procedure or maintenance session.

The information from location data source 238 can comprise position and orientation information associated with the manipulated catheter and/or sheath, or a portion thereof such as the tip of the device. In an embodiment where an impedance-based visualization, navigation, and mapping system 14 (e.g., ENSITE VELOCITY) is used as the source 238, the location data can comprise at least electrode coordinates (x, y, z) for specified electrodes on the catheter 406 or sheath 410. As will be described below, this data can be used, for example, to generate models and maps of anatomical structures that can be displayed on a display device 12, as well as to display on a display device 12 the location and orientation of the electrodes and/or the tip of the catheter 406 relative to an anatomical structure of interest.

The motor state model 230 contains information about the current states for each of the motors in the RCGS 10 (i.e., reflects the current physical states of the physical motors). States can include motor position, motor speed, tension (i.e., pull wire tension-see FIG. 6), and motor temperature. The motion server 232 is configured to interpret movement commands in a way so as to achieve the motor states specified in the motor state model 230. The motor server 232 also communicates information to the motor state model 230 that describes the current physical states of the motors in the RCGS 10.

The device state model 234 contains information regarding the catheter 406 and/or sheath 410, including data from any diagnostic or therapeutic sensor present on the distal end of the catheter 406. The information included within the device state model 234 can include, for example, the make, model and physical dimensions of the catheter 406 and sheath 410 as well as data specific to different sensors attached to the catheter 406, that can include, for example, ablation tip temperature, ablation energy output, and catheter irrigation flow rate. In an embodiment of the system 10 utilizing device cartridges 402, 404 having memory chips as detailed above, the device state model 234 can further include data representative of the attachment signal generated by the detecting means indicating a device cartridge 402, 404 is present.

The procedure model 236 contains the information received and processed during operation of the RCGS 10, including received location data 238, data from motor state model 230, data from device state model 234, and user input received from the user interface logic 226, which allows a user 224 to later review and analyze a procedure. The control logic 228 can be configured to generate a procedure model 236 in the memory 206 of the ECU 202, or in another embodiment, be configured to record a procedure model 236 on an external storage device (e.g., CD, DVD, USB mass storage device, external hard disk drive) using a wired or wireless data network. Further, the control logic 228 can be configured to receive user input directing transmission of a procedure model 236 to a specified or preconfigured location or group using a wired or wireless data network. The control logic 228 can also be configured to retrieve a procedure model 236 from the memory 206 or an external storage device for analysis and display it in a graphical user interface generated by the ECU 202.

In sum, the apparatus 222 implements a predetermined operating control strategy (i.e., higher level control algorithms) for the RCGS 10, as described in greater detail in U.S. application Ser. No. 12/751,843 filed Mar. 31, 2010 entitled "ROBOTIC CATHETER SYSTEM" that was referred to above. Based on user inputs, as well as other inputs as described herein, the apparatus 222 outputs actuation control signals 218 destined for the plurality of motors to achieve the desired catheter or sheath movements (i.e., translation, deflection or virtual rotation).

Figure 9:
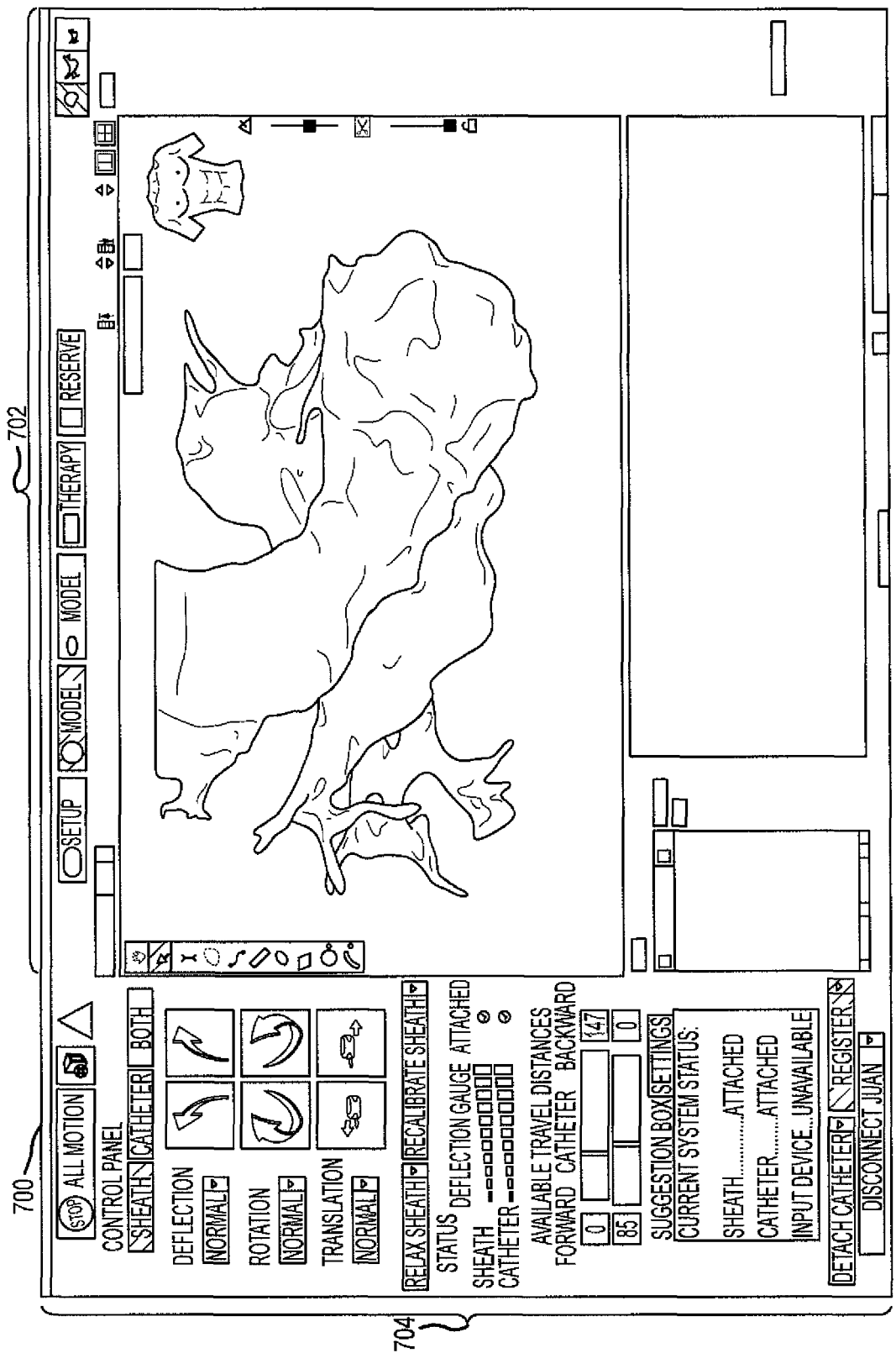
FIG. 9 is a diagrammatic view of the user interface window containing a visualization and mapping graphical user interface and a motion control and diagnostic display graphical user interface.

In an exemplary embodiment, and as briefly described above, the ECU 202, and the user interface logic 226, in particular, is further configured to generate a user interface window 700 configured for use in the control, operation, and/or configuration of the RCGS 10. The user interface window 700 is displayed on a display device 12 of the RCGS 10 and can include one or more graphical user interfaces for receiving input from a user 224 directed to one or more components of the RCGS 10 and for displaying diagnostic information related to the control and configuration of the RCGS 10, as described in detail below. The user 224 can use the input devices 102 of the input control system 100 to provide instructions to the ECU 202 relating to the display of the graphical user interfaces within the interface window 700, such as, for example, positioning each graphical user interface within the interface window 700, minimizing or hiding a graphical user interface, or resizing a graphical user interface. Once generated, the user interface logic 226 is configured to output the user interface window 700 to, for example, the input control system 100 where it can be displayed on the display device 104 thereof, as well as, in an exemplary embodiment, on one of the displays 12. FIG. 9 is a diagrammatic screen display of the user interface window 700 having a visualization and mapping graphical user interface 702 positioned to the right of a motion control and diagnostic display graphical user interface 704. As described above, the user 224 can direct the ECU 202 to reposition one or more of the graphical user interfaces, and the user interface 704, in particular, to appear, for example, along the upper, lower, right or left edges of the user interface window 700.

In an exemplary embodiment, the ECU 202 is configured to acquire a visualization and mapping graphical user interface 702 (mapping GUI) comprising a geometric model of an anatomical structure of interest and/or other information relating to, for example, the position and orientation of the catheter 406 and/or sheath 410. The mapping GUI 702 can also provide a graphical mechanism for the user 224 to provide inputs relating to various aspects of the RCGS 10, such as, for example, the visualization, navigation, and mapping system 14. The ECU 202 can be configured to acquire the mapping GUI 702 by generating the mapping GUI 702 itself, or by receiving the mapping GUI 702 (or some of the content presented by or comprising the mapping GUI 702) from another ECU of the RCGS 10 that is electrically coupled to and configured for communication with the ECU 202 (e.g., an ECU of the system 14 in an embodiment wherein the system 14 and electronic control unit 200 have separate and distinct ECUs). As set forth above, for purposes of clarity and illustration only, the description herein will be limited to an embodiment wherein the ECU 202 is configured to generate, acquire, or obtain all of the content presented by or comprising the mapping GUI 702, as well as to generate the mapping GUI 702.

Figure 10:
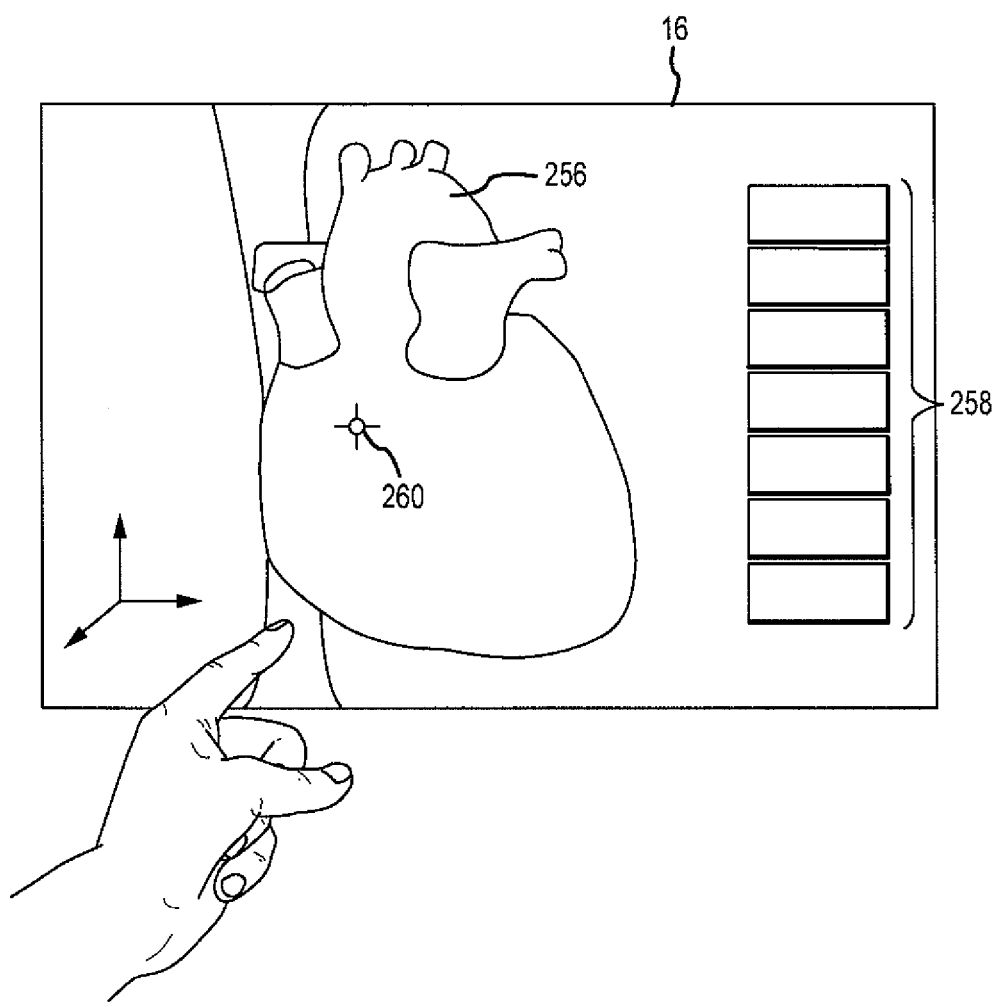
FIG. 10 is a diagrammatic view showing the visualization and mapping graphical user interface of FIG. 9 in greater detail.

FIG. 10 is a diagrammatic depiction of an exemplary embodiment of the mapping GUI 702. In this embodiment, the mapping GUI 702 includes a geometric anatomical model 256, which can represent a portion of a patient's anatomy (e.g., the patient's heart). The geometric model 256 can be generated by the ECU 202 based upon the data received from the location data source 238 (e.g., the visualization, navigation, and mapping system 14). The ECU 202 can then cause the model 256 to be displayed as part of the mapping GUI 702 on a display, such as, for example, one of the displays 12 and/or the display device 104 of the input control system 100. As illustrated in FIG. 10 and as briefly described above, the mapping GUI 702 can further include or present a variety of other information such as, for example, a current location of a catheter tip, shown at point 260. Additionally, the mapping GUI 702 can be configured to receive user inputs to direct execution of a variety of functions, including, for example only, panning, rotating, or zooming 3D objects and models (such as model 256) within the display, selecting and/or directing movement of the catheter or sheath, placing lesion markers, way points (i.e., as described above in order to specify a pre-planned movement for the catheter), virtual sensors, or automated movement targets and lines on or within the anatomic model 256. The user can provide these inputs to the mapping GUI 702 using, for example and without limitation, on-screen menus and/or on-screen buttons 258, or the like, of the mapping GUI 702 with which the user 224 interacts using, for example, one or more of the user input devices 102 of the input control system 100. Accordingly, in an exemplary embodiment, using the user input devices 102 in conjunction with the menu buttons 258 of the mapping GUI 702, the user can make selections or otherwise provide requested inputs (e.g., specifying values, selections between multiple options, etc.).

In an exemplary embodiment, the ECU 202 is configured to generate a motion control and diagnostic display graphical user interface 704 (control GUI 704) comprising a plurality of on-screen buttons for selecting and/or directing movement of the catheter 406 or sheath 410, selecting and/or controlling therapeutic or diagnostic procedures, and calibrating the catheter 406 or sheath 410. The control GUI 704 is also configured to display several diagnostic elements providing information regarding the components of the RCGS 10, such as, for example, information from the motor state model 230 and device state model 234. The control GUI 704 can be configured to operate in either a physician mode while the user performs a therapeutic or diagnostic procedure or a maintenance mode while the RCGS 10 components are being tested or configured.

The maintenance mode of the control GUI 704 can be used when the display of diagnostic information about the components of the RCGS 10 is desired by the user 224, such as, by way of example, when configuring a system, attempting to identify a malfunctioning component, or performing routine maintenance. This diagnostic information can comprise information that would not ordinarily be desired or needed by the user 224 during the normal operation of the RCGS (e.g., during the physician mode when a procedure is being performed). In addition to diagnostic information that can be displayed in a diagrammed format during physician mode, which is described below, the diagnostic information displayed in maintenance mode can include pull wire tensions, absolute and relative position values for the fingers 316, 318, 320, and 322, absolute and relative position values for the manipulation bases 308 and 310, motor temperatures from the motor state model 230 as well as data from the device state model 234, such as catheter 406 and/or sheath 410 make, model, and physical dimensions.

The physician mode of the control GUI 704 can be utilized when a user is performing a diagnostic, therapeutic, or other procedure where a comprehensive display of diagnostic data cannot be necessary. The physician mode can be configured to display diagnostic data related to the translation and deflection of the catheter 406 and/or sheath 410 as well as the presence of an attached catheter 406, sheath 410, or input device 102 in a graphical form that can be intuitively understood by a user 224. For example, and as described in greater detail below and illustrated in FIG. 11, the control GUI 704 can contain a graphical position display 706 diagramming the absolute and relative position data of the manipulation bases 308 and 310 to indicate the amount of translational movement remaining, or a graphical deflection display 708 diagramming the absolute and relative position data of the fingers 316, 318, 320, and 322 to indicate the amount of deflection present in the distal end of a catheter 406 and/or sheath 410. The physician mode can further include control limitations programmed into the control logic 228 of the ECU 202 preventing some types of movement described below, such as, by way of example, customized discrete movement distances exceeding a preprogrammed size, or continuous movement when the P&O of the distal tip of a catheter 406 or sheath 410 are within a preprogrammed distance of a structure depicted in the geometric model 256.

Figure 11:
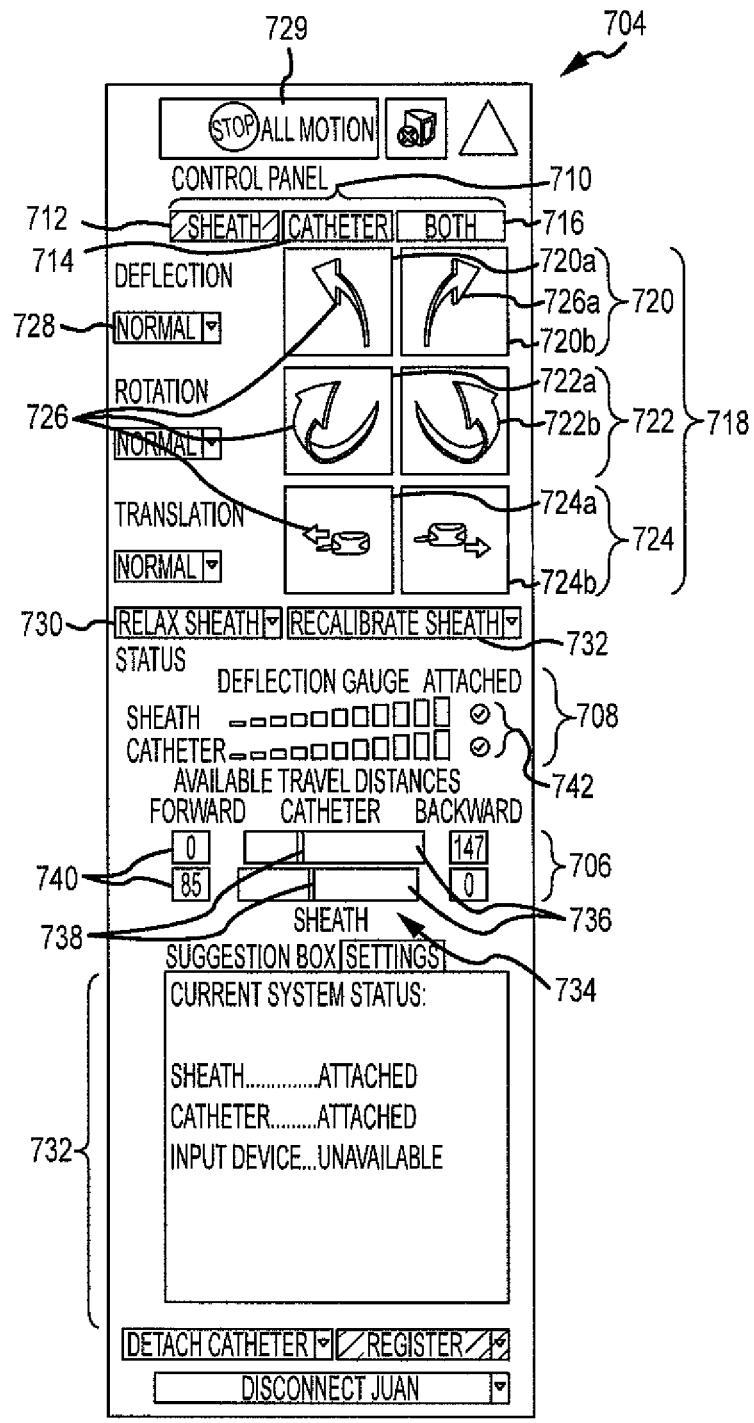
FIG. 11 is a diagrammatic view showing the motion control and diagnostic display graphical user interface of FIG. 9 in greater detail.

An exemplary embodiment of the control GUI 704 is shown in detail in FIG. 11, which allows for, among other things, control of the movement of both the catheter 406 and an associated sheath 410 through the use of a series of on-screen buttons and drop-down menus allowing the physician to select a device and enter input directed to the device, such as input directed to translating, deflecting, or rotating the selected catheter 406 and/or sheath 410 as well as initiating calibration of the device. Although on-screen buttons and drop-down menus are utilized to facilitate user input in the described embodiment, alternative graphical user interface input means known to those skilled in the art, such as, by way of example, radio buttons or check boxes can be utilized without departing from the scope of the present disclosure. Further, the on-screen buttons of the graphical user interfaces of the described embodiments can utilize an active state display and an inactive state display, where the inactive state display is depicted during periods when the function or device associated with the button has not been selected by the user 224, while the active state display is depicted when the function or device has been selected by the user 224. The active state display can be depicted in a manner contrasting with buttons shown with an inactive state display in order to allow the user 224 to distinguish active buttons from inactive buttons. The active state display can contain a lighter shade of the button background color than an inactive state display, but alternative embodiments achieving a contrasting appearance through the use of other means, such as changing the color, opacity, size, or orientation of one or more visual elements of a button or by adding a visual effect such as animation or flashing remain within the scope of the present disclosure.

In the described embodiment, the control GUI 704 allows the user 224 to control the sheath 410, catheter 406, or both through the device buttons 710. As shown in FIG. 11, the control GUI 704 displays a sheath control button 712, a catheter control button 714, and a dual control button 716. Activating the sheath control button 712 or the catheter control button 714 allows the user 224 to control only the sheath 402 or catheter 404, respectively. The dual control button 716 allows the user 224 to control both the catheter 406 and the sheath 410 simultaneously. When one of the device buttons 710 are selected by the user 224, any previously selected device button 710 becomes inactive.

Simultaneous control of both the catheter 406 and sheath 410 can be accomplished in an alternative embodiment when control GUI 704 contains only a sheath control button 712 and a catheter control button 714 and while allowing both buttons to be active at the same time.

The control GUI 704 allows the user 224 full control of the selected device through the use of a series of control buttons 718 including deflection buttons 720, rotation buttons 722, and translation buttons 724. The control buttons 718 allow the user to actively navigate the catheter through a combination of deflection, rotation, and translation movements. The control buttons 718 of the described embodiment have two buttons for each of the deflection, rotation, and translation movements, with each of the two buttons associated with the individual movement types allowing movement in opposite directions. For example, rotation of the active device can be accomplished in a clockwise manner through the use of a first rotation button 722a while rotation in a counter-clockwise manner is accomplished through the use of the other, or second rotation button 722b. Similarly, translational movement of the active device in the distal or proximal directions (i.e., further insertion or withdrawal of the device) can be accomplished with the use of a first translational button 724a and a second translational button 724b, and increasing or decreasing the deflection of the distal tip of the active device can be accomplished with a first deflection button 720a and a second deflection button 720b.

Each control button 718 can have an action icon 726 disposed thereon visually identifying the action of the button 718. In an exemplary embodiment, the action icon 726 uniquely identifies the action of each control button 718, yet maintains a common identifier with the control button 718 effecting the same type of movement in the opposite direction (i.e., both control buttons corresponding to deflection, for example, will have icons that have at least a common identifier to indicate they correspond to the same movement action). For example, in the illustrated embodiment each deflection button 720 in FIG. 11 has a deflection icon 726a comprising a curved arrow where the arrows of each icon 726a are the same in all respects but for the direction of the curve, which is indicative of the direction of deflection corresponding to that particular control button. While the curved arrow of the icons 726a of the deflection control buttons 720 are very similar to each other, they are substantially different than the arrows used in the action icons 726 on the rotation buttons 722 and the translation buttons 724. For example, the action icon 726 of the rotation buttons 722 comprises a nearly circular arrow where the direction of the arrow head indicates either clockwise or counterclockwise motion. Similarly, the action icon 726 of the translation buttons 724 comprise a stylized depiction of a device cartridge 400 accompanied by an arrow pointing in the direction of translation. In an alternative embodiment, the deflection icons 726a can additionally or alternatively contain a plus or minus symbol to indicate whether activating the control button 718 would increase or decrease the deflection of the selected device.

When the dual control button 716 is selected and the catheter and sheath are deflected in different directions the deflection control buttons 720 become non-functional, which can be indicated in an exemplary embodiment by a visually distinctive change in the display of the deflection control buttons 720. For example, non-functional deflection control buttons 720 can be displayed with a darker color shade, a varied opacity, or an additional visual element such as an "X."

The control buttons 718 can allow the physician to cause the RCGS 10 to perform either a discrete movement or a continuous movement. A discrete movement allows the user 224 to direct the RCGS 10 to actuate the active device through a known displacement with a single input, or click, regardless of the length of time the control button 718 is actuated by the user 224. Input received from a control button 718 when discrete movement has been selected causes the ECU 202 to translate the input into a motor actuation command instructing the actuation unit 600 to move the active device a specific distance. In an exemplary embodiment, continuous movement directs the ECU 202 to generate a motor actuation command starting movement when the control button 718 is first selected (e.g., clicked) by the user and ceasing movement when the control button is released (e.g., the click is released). In an alternative exemplary embodiment, a continuous movement input can be communicated to the ECU 202 by activating (e.g., clicking) a control button 718 for a length of time longer than a preprogrammed threshold. For example, a control button activated for more than one second could be interpreted by the ECU 202 as indicating a continuous rather than discrete movement, which would be effected until the control button 718 was released. In such an alternative exemplary embodiment, the time threshold indicating continuous movement can correspond to the time taken by the actuation unit 600 to effect a discrete movement. For example, a three millimeter discrete movement taking three seconds to complete would require a continuous activation or click of three seconds before the ECU 202 would interpret the user input as directing continuous movement. Although two embodiments of continuous movement control have been discussed, any number of other ways to initiate or cease continuous movement can be used and remain within the spirit and scope of the disclosure.

In the described embodiment, the user 224 can select a movement type from a movement type menu 728 that, in the described embodiment, can take the form of a drop-down menu containing a plurality of discrete movement distances and, in an exemplary embodiment, a continuous movement option. Each of the deflection, rotation, and translation control buttons 720, 722, 724 can have a corresponding movement type menu 728 allowing the user 224 to select different movement types for deflection, rotation, and translational movement inputs. The discrete movement distances can be displayed as a physical distance (e.g., 1 mm) or as subjective descriptors, such as, for example, "minor," "normal," and "major," where each subjective descriptor has a corresponding distance preprogrammed into the control logic 228 of the ECU 202. In an exemplary embodiment provided for illustrative purposes only, the preprogrammed distances corresponding to the "minor," "normal," and "major" descriptors are one, three, and five millimeters for translational movements and three, five, and seven degrees for deflection and rotational movements. The movement type selected by the user 224 can appear on the menu 728 to indicate the active movement type.

In an alternative embodiment not shown, the movement type menu can contain an option allowing the user 224 to utilize a customized discrete movement distance created during the procedure or created previously and loaded from the memory of the ECU 202. A customized discrete movement can be created in one embodiment by including a "custom" option within the movement type menu 728. When the user 224 selects the custom option, the ECU 202 can be programmed to generate a value input field within the control GUI 704 where the value input field is configured to receive a numerical input representing the size of the customized discrete movement. The numerical input can be received by the ECU 202, which can then include the customized discrete movement in the movement type menu 728. Alternatively, the physician or user can be presented with a list of possible values from which the physician can select desired values for each discrete movement.

In another embodiment, the ECU 202 can further be configured to allow a user 224 to save and retrieve customized discrete movement distances to/from the memory 206 of the electronic control system 200 or an external memory device. Control GUI 704 can be configured to prompt a user 224 to save a customized discrete movement distance at the time of its creation or later (e.g., at system shutdown) by displaying a prompt window within the user interface window 700. The prompt window can be configured to allow the user 224 to enter input electing or declining to save the customized discrete movement distance and, when electing to save, to select either the memory 206 or an external memory device. The ECU 202 can be configured to retrieve a saved customized discrete movement distance by configuring the movement type menu 728 to contain a "load" option, wherein selection of the load option directs the ECU 202 to search the memory 206 and any external memory devices in electrical communication with the ECU 202 in order to acquire and display a listing, for example, as part of the movement type menu 728 or in a separate window within the interface window 700, of customized discrete movement distances from which the user 224 can select.

In an embodiment of the invention, each of the control buttons 718 can be depicted in the control GUI 704 by the ECU 202 in the active state while the motion corresponding to that button is being effected by the actuation unit 600, which, when discrete movement is selected, cannot be complete when the user activation of the control button 718 ceases. Continuing to display the control button 718 in the active state provides a ready visual indicator that the selected device continues to move. In this manner, the user can easily verify whether the catheter 406 or sheath 410 are in motion, as well as the particular nature of the motion, thereby minimizing the chance that the catheter 406 or sheath 410 would be in motion unbeknownst to the user 224.

In an exemplary embodiment of the invention, the control GUI 704 can contain a stop motion button 729 allowing a user 224 to direct the ECU 202 to cease all movement of the attached catheter 406 and/or sheath 410. In an embodiment where the input control system 100 is configured to receive audio user input (e.g., verbal commands) the input logic 226 of the ECU 202 can be configured to interpret an audio user input as activating the stop motion button 729, or otherwise issuing one or more motor actuation commands stopping movement of any attached devices.

The control GUI 704 can also contain a relax button 730 allowing the user to direct the ECU 202 to release any deflection present in the selected catheter 406 or sheath 410 thereby returning the device to an undeflected position. The relax button 730 allows the user 224 to prepare the device for withdrawal from the patient or a work area with a single input rather than repeatedly activating the deflection control buttons 720 to straighten the device. The relax button 730 in an exemplary embodiment displays the name of the device that will be relaxed when the button is activated. Further, in an exemplary embodiment, the relax button 730 can take the form of a drop down menu wherein clicking within the drop down menu allows the user 224 to select between devices available for relaxation. As with the movements initiated using the control buttons 718, the relax button 730 can be displayed in the active state when device movements effected by the button continue.

In an embodiment, the control GUI 704 can further contain a calibration button 732 allowing a user 224 to direct the ECU 202 to initiate a user-guided configuration routine for attaching, detaching, or replacing a catheter 406 or sheath 410. The user-guided configuration routine is described in greater detail below.

In an exemplary embodiment not shown, in addition to or instead of the functionality described above, the control GUI 704 can further allow the user 224 to control a diagnostic or therapeutic procedure, such as, for example, an ablation procedure. In an exemplary embodiment, the control GUI 704 contains an ablation power button allowing the physician to control the delivery of ablative energy from an ablation electrode mounted on the catheter. The control GUI 704 can further contain an ablation power selector that allows the user to adjust the rate at which energy is emitted from the ablation device. The power selector can take the form of a slider bar with an adjustable element the physician moves along the length of the bar to adjust the power. Alternatively, the power selector can be depicted as a numerical value representing, for example, the magnitude of the ablation power being delivered, with an increment control button that increases the power output, and a decrement control button decreasing the power output.

In an exemplary embodiment wherein the catheter 406 is an irrigated catheter, the control GUI 704 can further contain an irrigation control interface allowing the physician to start or stop irrigation as well as adjust the fluid flow rate when irrigation is in progress. The irrigation control interface can include an on/off toggle button used to start or stop irrigation and a flow rate selector. In one embodiment, the toggle button includes a static label indicating the button controls the irrigation function as well as a button display element that can be displayed in the active state during irrigation and in the inactive state when irrigation has ceased. In an exemplary embodiment, the flow rate selector preferably includes a flow rate indicator and an adjustment interface. In one embodiment, the flow rate indicator is a numerical value display showing a quantitative value or a percentage value of the potential flow rate. The adjustment interface can include an increment and decrement control button, the increment control button increasing the flow rate by a predetermined amount and the decrement control button reducing the flow rate by a predetermined amount. Alternatively, the adjustment interface can further include a flow rate menu, such as, for example, a drop down menu, allowing the physician to select one of several menu flow rates without needing to repeatedly click the increment or decrement control buttons. Once a menu flow rate has been selected, the physician can use the increment and decrement control buttons to make any desired adjustments away from the menu flow rate.

The control GUI 704 can further contain an information box 732 allowing for the display of procedure related information by the ECU 202, such as a listing of attached catheter and sheath devices as well as a listing of available input devices 102. The information box can further display error messages or messages requesting user action generated by the ECU 202.

As briefly described above, in an exemplary embodiment, the control GUI 704 can contain the graphic position display 706 diagramming the position and available translational movement of the catheter and/or sheath, as well as the graphic deflection display 708 diagramming the amount of deflection present in the catheter 406 and/or sheath 410.

Graphic Position Display.

The graphic position display 706 is created by the ECU 202 as a depiction of the absolute and relative position data from the motor state model 230 that is easily interpreted. The graphic position display 706 can illustrate the available distal and proximal translational movement of the catheter 406 and/or sheath 410, which is determined by the absolute position of each with the track 356 and position of the manipulation base of the other device. For example, the translational movement of the sheath manipulation base 310 is constrained in the distal direction by the end of the track 356 on which the sheath manipulation base 310 translates. In the proximal direction, the translational movement of the sheath manipulation base 310 is constrained by the position of the catheter manipulation base 308 within the track 356 because both the catheter and sheath manipulation bases 308, 310 travel within the same track 356, and the catheter passes through the sheath, requiring the catheter manipulation base 308 be positioned proximal to the sheath manipulation base 310. The graphic position display 706 diagrams the relative positions of the catheter and sheath manipulation bases 308, 310 within the track 356 and relative to one another to produce a diagnostic display that a user 224 can quickly refer to determine the available translational movement of a catheter or sheath and absolute positions of both devices to illustrate any limitations.

In the illustrated embodiment, the control GUI 704 can contain a graphic position display 706 for each of the catheter 406 and sheath 410. The graphic position display 706 can have an available travel indicator 740 for both proximal and distal directions showing the available translational movement distance in each direction as well as a track position indicator 734 showing the manipulation base position within the track 365. In the illustrated embodiment, the available travel indicators 740 display a numerical value representing the available translational movement in a distal or proximal direction for the catheter 406 or sheath 410. The numerical value need not correspond to any specific unit of measure, such as centimeters or millimeters, but rather can be a percentage or arbitrary division of the available travel.

In an exemplary embodiment, the track position indicators 734 are represented by a range bar 736 displaying a position stripe 738. The position stripe 738 is displayed at a location within range bar 736 such that the position stripe 738 divides the range bar into segments whose size correspond to the remaining travel distance in their respective direction. Thus, when a device is moved in the forward direction, the position stripe 738 moves left in the range bar 736 depicted in FIG. 11, thereby decreasing the segment of the range bar 736 on the left, or the distal travel side, of the position stripe 738. When both a catheter 406 and sheath 410 are present, the range bars 736 of the catheter 406 and sheath 410 can be displayed with a horizontal offset between the two range bars 736 such that when the position stripe 738 of the catheter moves to the left of the position stripe 738 of the sheath, then the distal tip of the catheter 406 extends beyond the distal end of the sheath 410, thereby providing a quick visual reference for the of the exposure of the distal end of the catheter 406.

In an exemplary embodiment, the control GUI 704 can also display a zero travel indicator and a collision indicator as part of the graphic position display 706. The zero travel indicator can be displayed when either the sheath or catheter manipulation bases 310, 308 have reached the end of track 356 and can no longer travel in the proximal direction for the catheter 406 and distal direction for the sheath 410. The zero travel indicator of an exemplary embodiment is displayed as a changing background color in the available travel indicator 740. Acceptable alternative embodiments of the zero travel indicator include a separate icon normally hidden that becomes displayed, or an icon normally displayed in an inactive state that can change to an active state, when the zero travel condition exists.

The collision indicator is displayed when there is no more available translational movement distance between the catheter manipulation base 308 and the sheath manipulation base 310 within the track 356, and occurs when the two manipulation bases 308, 310 are adjacent. Thus, referring now to FIG. 3a, the sheath manipulator 310 cannot translate within tack 356 in a proximal direction because it would contact, or collide with, the catheter manipulation base 308. Similarly, the catheter manipulation base 308 cannot translate within track 356 in a distal direction because it would contact, or collide with, the sheath manipulation base 310. The collision indicator alerts the user 224 to this condition, and in an exemplary embodiment, is displayed as an altered background color of the available travel indicator 740 in both the distal direction for the catheter graphic position display 706 and the proximal direction of the sheath graphic position display 706. Acceptable alternative embodiments of the collision indicator include a separate icon normally hidden that becomes displayed or an icon normally displayed in an inactive state that can change to an active state when the collision conditions exist.

Graphic Deflection Display.

In an exemplary embodiment, graphic deflection display 708 is generated by the ECU 202 as a graphic depiction of the amount of deflection present in the distal end of a catheter 406 or sheath 410. The ECU 202 interprets the absolute and relative position data of the motors 342, 344, 346 and 348 controlling the fingers 316, 318, 320, and 322 from the motor state model 230 and the steering wire tension data from the strain gauges associated with the fingers 316, 318, 320, and 322 to determine the distal tip deflection. The graphic deflection display 708 allows the user 224 to ascertain the amount of deflection in a device without interpreting the individual diagnostic data values discussed above, thereby providing a meaningful reference for navigation of a catheter 406 and/or sheath 410.

In an exemplary embodiment, the graphic deflection display 708 is shown as a series of graduated columns or bars that change color as the distal end of the device is increasingly deflected. As a device is deflected, the graduated columns incrementally change from an idle color to an active color, such that the smallest bar changes first followed by the next smallest bar, and so on and so forth. The bars continue to change to the active color as more deflection occurs until the device is at maximum deflection and all of the bars in the deflection gauge have been changed to the active color. As the deflection is decreased, the bars change back to the idle color. Thus, the extent of the progression of the active color through the series of bars serves as a visual identifier of the extent of the device's deflection. Alternatively, the graphic deflection display 708 can be depicted as a numerical percentage, a rectangular bar whose color progressively changes, or some similar indicator.

Device Attachment Status Display.

In an embodiment having a detection means generating an attachment signal, as previously described, the ECU 202 can generate an attachment status icon 742 for display within the control GUI 704 representative of the attachment signal indicating that a device (e.g., a catheter or sheath) is attached to the RCGS 10. By way of example, the control GUI 704 depicted in FIG. 11 contains two attach status icons 742 displayed as a checkmark icon beneath the label "attached" for each of the catheter 406 and sheath 410, indicating that each device is attached. Should one device not be attached, the corresponding attach status icon 742 would be displayed as a red "X" or other symbol recognized as indicating a negative condition.

User-Guided Configuration Routine.

In an exemplary embodiment, and as briefly described above, the ECU 202 is further configured to perform or execute a user-guided configuration routine. The routine can be stored in the memory 206 of the ECU 202 and executed by the processor 204 thereof. The user-guided configuration routine leads the user 224, such as, for example, a physician or clinician, through the catheter 406 and sheath 410 attachment and configuration process, as well as the detach process.

For purposes of context, the catheter 406 and sheath 410 are typically inserted into and maneuvered through the patient's vasculature until the distal portions thereof are in close proximity to the procedure area, commonly within the heart. Once the catheter 406 and sheath 410 are in position, they must be both attached to the RCGS 10 and configured to allow the RCGS 10 to accurately move the attached catheter 406 and/or associated sheath 410.

The user-guided configuration routine can be executed by the ECU 202 in response to user input from the calibration button 732 of the control GUI 704. The user-guided configuration routine can also be employed when a catheter 406 or sheath 410 must be replaced during a procedure due to breakage or defective performance, or when the system is recovering from an emergency condition, such as a power outage. While the user-guided configuration routine is being performed, it maintains exclusive control over the RCGS 10 and any user input received by the control buttons 718 of the control GUI 704 while the user-guided configuration routine is in process will not result in any movement of the catheter 406 and/or sheath 410. The ECU 202 generates a configuration graphical user interface 800 (configuration GUI 800) within the user interface window 700 for displaying status information regarding the configuration process, prompting the user for input, and receiving user input.

In an exemplary embodiment, the ECU 202 can be configured to execute a plurality of user-guided configuration routines where each routine contains a number of configuration steps selected to address a specific instance requiring calibration. For example, a device replacement routine can contain configuration steps directed to detaching an existing catheter 406 or sheath 410 from the RCGS 10 and attaching a new catheter 406 or sheath 410 as a replacement. Such a configuration routine would omit unnecessary steps that are part of a larger configuration routine (such as, for example, detaching a catheter when none is attached), allowing the configuration process to be performed quickly and efficiently. In such an embodiment, the ECU 202 can display the plurality of user-guided configuration routines within a drop-down menu associated with the calibration button 732 of the control GUI 704 that can be executed either at the start of a procedure (e.g. a therapeutic or diagnostic procedure using the RCGS 10) or during an on-going procedure. In another embodiment, the configuration routine steps can be grouped into modules, where each module contains a collection of configuration steps commonly performed together.

Configuration Graphical User Interface.

Figure 12:
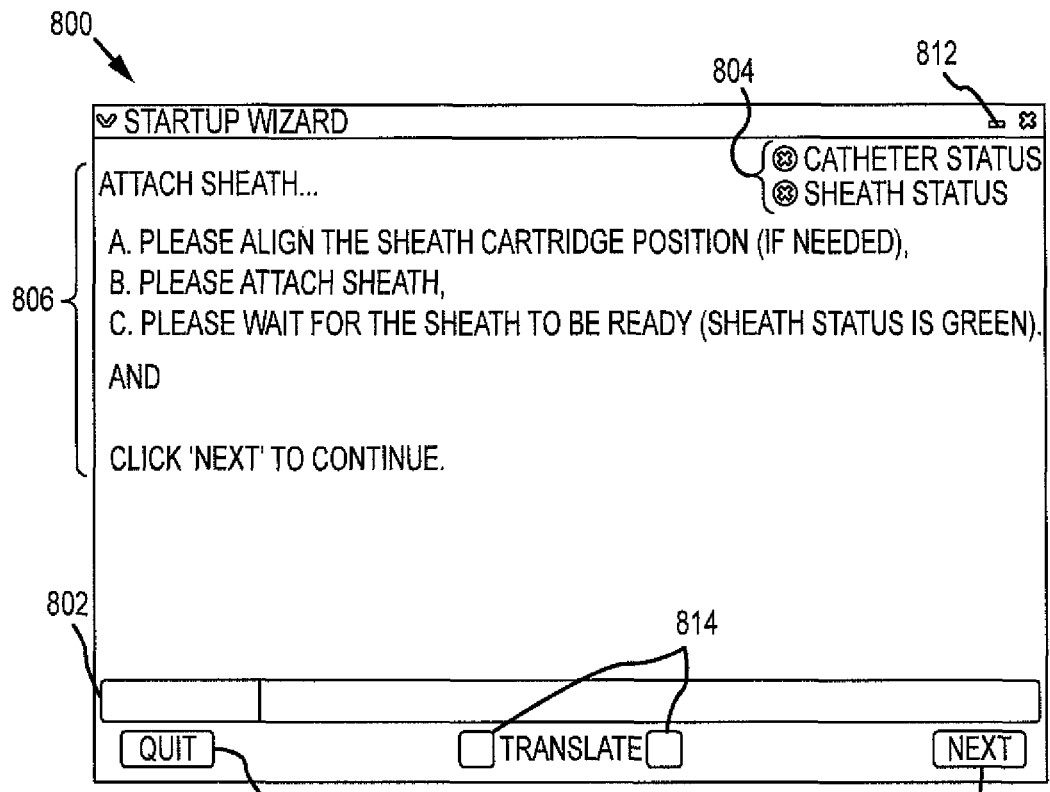
FIG. 12 is a diagrammatic view of the configuration graphical user interface illustrating a first exemplary layout.
Figure 13:
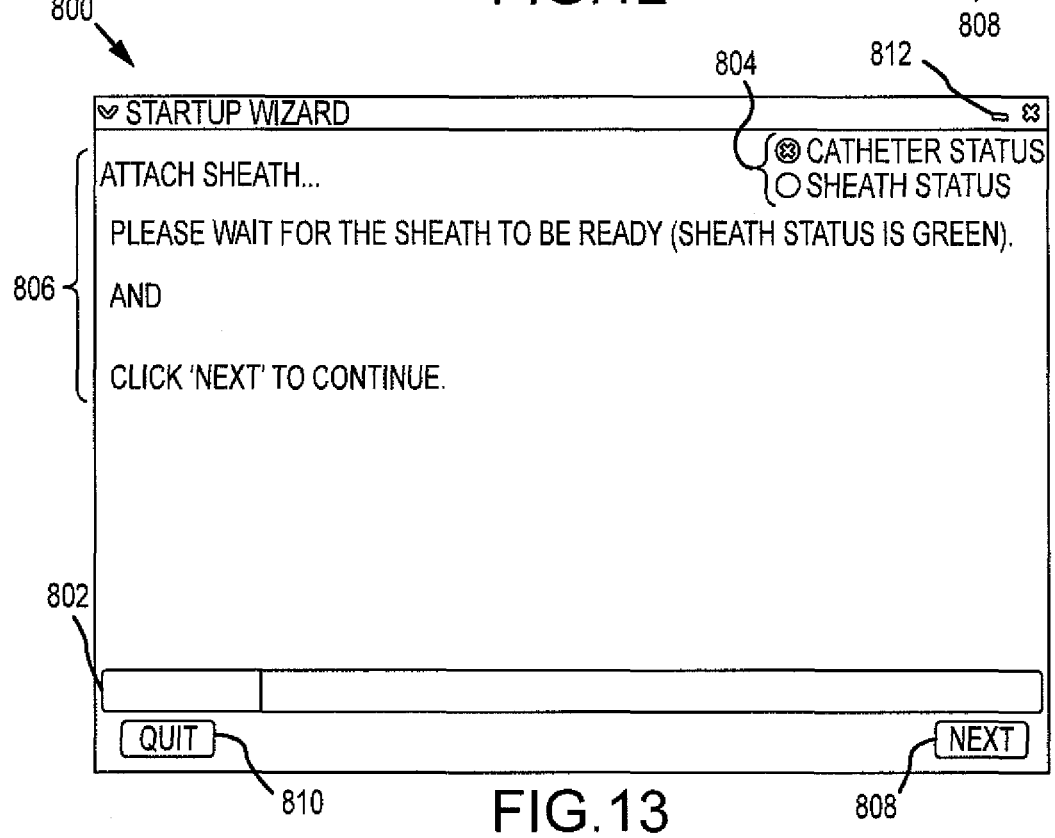
FIG. 13 is a diagrammatic view of the configuration graphical user interface illustrating a second exemplary layout.

As generally illustrated in FIGS. 12 and 13, an exemplary embodiment of the configuration GUI 800 can contain, among other things, several status indicators, including a status bar 802, a status indicator icon 804, a status statement 806, and a plurality of input buttons for user interaction.

In an embodiment consistent with the present disclosure, a status bar 802 can be used to display a visual representation of the progress of the system 10 through the configuration step underway. The configuration GUI 800 can also contain a status indicator icon 804 that visually indicates to the user whether the labeled device has or has not been configured, as well as when configuration is underway. The status indicator icon 804 can be accompanied by a label, but in some embodiments the icon's visual depiction alone can be sufficient to identify the corresponding device. The visual depiction of the icon 804 changes from an unconfigured indicator to a working indicator when the device is being attached, to a ready indicator that is displayed once the device is fully configured. The configuration GUI 800 can also contain a status statement 806 that can be used to display the current step of the configuration process as well as any required user action. The status statement 806 can also be used to display messages for device failures or suggestions as the appropriate action for the user to take to remedy a failure.

The configuration GUI 800 further contains user input buttons allowing the user to advance through the configuration steps, exit the process, or provide configuration input. The user input buttons can be a navigation button 808 allowing the user to advance from one configuration step to the next. The user input buttons can also be an exit button 810 that exits the automatic configuration process. In an exemplary embodiment, the exit button 810 is present in all phases of the configuration process and allows the user to exit the user-guided configuration routine at any time. The user input buttons can also be a hide button (not shown). The hide button allows the user to remove the configuration GUI 800 from view to allow access to the other graphical user interfaces displayed within the interface window 700. Alternatively, the hide button can be replaced with a minimize button 812 commonly found in windowed computing applications. The user input buttons can further comprise a configuration button 814 that supplies information used in configuring the catheter 406 and/or sheath 410, such as manually adjusting a manipulation base 308, 310.

In an exemplary embodiment, the configuration GUI 800 can include an input button allowing the user 224 to indicate the number and type of devices to be calibrated. For example, the input button could take the form of a drop down menu having the options of "catheter," "sheath," and "dual," where selection of the "catheter" or "sheath" options directs the ECU 202 to only calibrate a catheter 406 or sheath 410, respectively. Selection of the "dual" option, however, would direct the ECU 202 to calibrate both the catheter 406 and sheath 410 devices. In such an embodiment, the selection can be indicated by the ECU 202 including an icon or other display element in the configuration GUI 800 reflecting the selection.

User-Guided Configuration Routine Steps.

The steps of the user-guided configuration routine and the individual modules can be arranged in several different combinations depending on the state of the RCGS 10 and the action desired by the user 224. The steps of the device detach module 1000, the sheath attachment module 2000, and the catheter attachment module 3000, described in detail below, executed sequentially are consistent with the configuration of an RCGS 10 having both a catheter 406 and sheath 410 previously attached that must be replaced. In alternative embodiments, described in detail below, a subset of the enumerated configuration steps can be utilized to perform more limited calibration to address specific situations. By way of example, a subset of the described configuration steps can be used to replace and calibrate only a catheter 406 device during a procedure.

Device Detach Module.

Figure 14:
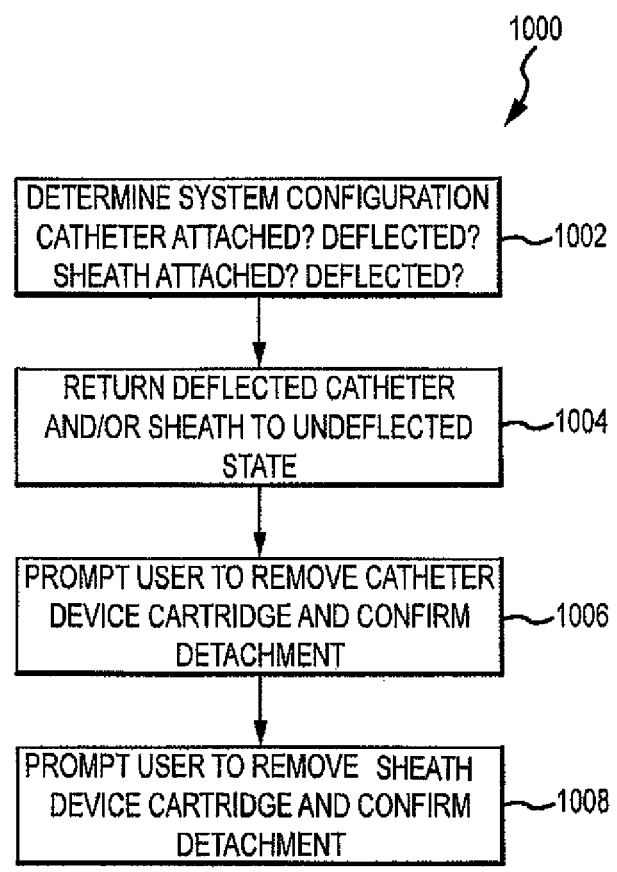
FIG. 14 is a flow chart illustrating an exemplary embodiment of a portion of the user-guided configuration routine logic directing the detachment of a medical device.

As shown in FIG. 14, the device detach module 1000 of an exemplary embodiment of the user-guided configuration routine begins with a step 1002 of determining the current configuration of the RCGS 10. The ECU 202 can determine the configuration of the RCGS 10 by accessing the current diagnostic information, such as the motor state model 230 and device state model 234. Step 1002 can include determining whether a catheter 406 and or sheath 410 are attached to the RCGS 10. In an embodiment wherein a detection means is utilized as part of the manipulation bases 308, 310, step 1002 can be accomplished by ECU 202 referencing the attachment signal from the detection means of manipulation bases 308, 310. Alternatively, step 1002 can be accomplished by referencing steering wire tension data received in the motor state model 230.

When a catheter 406 or sheath 410 is present and in a deflected state, the described embodiment of the user-guided configuration routine continues with a step 1004. When a catheter 406 is not present or is not deflected, the user-guided configuration routine relaxes (i.e. straightens) the sheath 410, described below. Step 1004 comprises returning the catheter 406 to an undeflected state, which the ECU 202 can accomplish by issuing motor commands to the motor server directing that fingers 316, 318, 320, 322 be positioned such that each of the corresponding steering wires, as represented in the motor model state 230, are not tensioned.

When a sheath 410 is present and in a deflected state, the described embodiment of the user-guided configuration routine can continue step 1004 by returning the sheath 410 to an undeflected state, which the ECU 202 can accomplish by issuing motor commands to the motor server directing that fingers 316, 318, 320, 322 be positioned such that each of the corresponding steering wires, as represented in the motor model state 230, are not tensioned.

While the catheter 406 and sheath 410 are being returned to an undeflected state the configuration GUI 800 displays a summary message as the status statement 806 and updates the status bar 802.

The described embodiment of the user-guided configuration routine continues with a step 1006. Step 1006 comprises the ECU 202 generating a status statement 806 prompting the user 224 to remove a catheter device cartridge 402, if present, and waiting for confirmation that the attached catheter device cartridge 402 has been removed. Confirmation can be accomplished by receipt of user input through a navigation button 808, illustrated in FIG. 12, or alternatively, by ECU 202 accessing the attachment signal generated by an attachment means of the manipulation base 308.

The illustrated embodiment of the user-guided configuration routine continues with step 1008 that comprises the ECU 202 generating a status statement 806 prompting the user 224 to remove a sheath device cartridge 404, if present, and waiting for confirmation that the attached sheath device cartridge 404 has been removed. As with step 1006, confirmation can be accomplished by receipt of user input through a navigation button 808, or alternatively, by ECU 202 accessing the attachment signal generated by an attachment means of the manipulation base 310.

Sheath Attachment Module.

Figure 15:
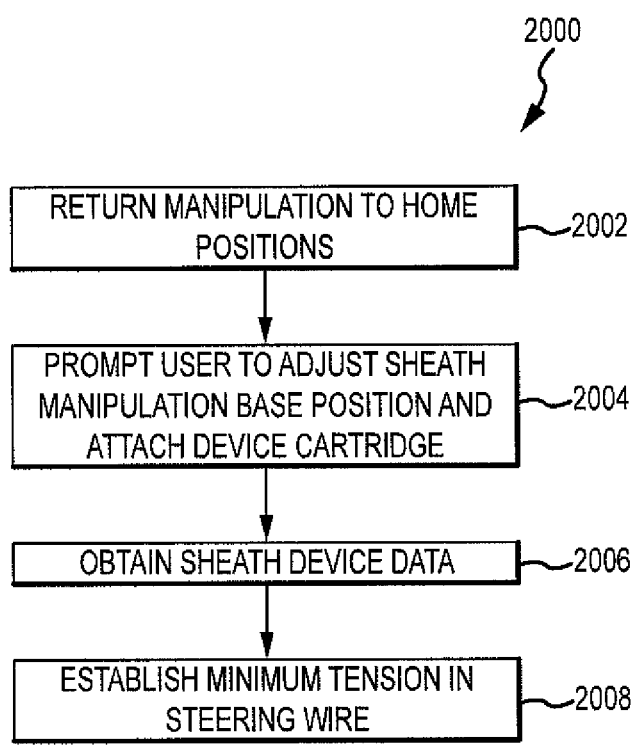
FIG. 15 is a flow chart illustrating an exemplary embodiment of a portion of the user-guided configuration routine logic directing the attachment of a sheath.

The described embodiment of the user-guided configuration routine can contain a sheath attachment module 2000, illustrated as a block diagram in FIG. 15. The sheath attachment module 2000 begins with step 2002, which comprises the ECU 202 generating a plurality of actuation control signals 210 and communicating them to the motor server 232 to return the manipulation bases 308, 310 to home positions. While the user-guided configuration routine is repositioning the catheter and sheath manipulation bases 308, 310 to their respective home positions, the configuration GUI 800 can display a status statement 806 and a status bar 802.

The described embodiment of the sheath attachment module 2000 continues with step 2004. Step 2004 comprises the ECU 202 generating a status statement 806 prompting the user 224 to input any necessary translational position adjustments of the sheath manipulation base 310 and to attach a sheath device cartridge 404, and waiting for confirmation that the sheath device cartridge 404 has been attached. User input directing an adjustment to the position of the sheath manipulation base 310 can be received by configuration buttons 814 and can be translated by ECU 202 into actuation control signals 210. Confirmation that a sheath device cartridge 404 has been attached can be accomplished by receipt of user input through a navigation button 808, or alternatively, by ECU 202 accessing an attachment signal generated by an attachment means of the manipulation base 310.

The described embodiment of the sheath attachment module continues with step 2006. Step 2006 comprises the ECU 202 obtaining sheath device data, which can be accomplished in an embodiment by accessing the memory chip of the sheath device cartridge 404 to retrieve the encoded sheath data described above, such as, by way of example, the sheath physical dimensions. In such an embodiment, the memory chip is accessed through an electrical manipulator head and is transmitted to the ECU 202 through a signal or data transmission means such as a system bus or network. Where a sheath device cartridge 404 lacks a memory chip, or the manipulation base 310 lacks an electrical manipulator head, the ECU 202 can prompt the user 224 through a plurality of status statements 806 to input the sheath device data by way of one or more user input buttons. In an exemplary embodiment, the sheath device data can be stored in the computer readable storage media of the electronic control system 200 and can be accessed by the ECU 202.

While the sheath device data is being accessed, the status indicator icon 804 associated with the sheath is displayed as a working indicator (not shown), and when the sheath device data has been successfully acquired by the ECU 202, the ECU 202 can display a status statement 806 informing the user of successful attachment and the status indicator icon 804 is displayed as a ready indicator within the configuration GUI 800.

The described embodiment of the sheath attachment module continues with step 2008, which comprises establishing a minimum tension for each of the sheath steering wires to place the sheath 410 in a substantially undeflected orientation. The minimum tension for each steering wire can be accomplished by the ECU 202 by generating actuation control signals 210 directing movement of the fingers 316, 318, 320, 322 and by ECU 202 monitoring the motor state model 230 for changes in steering wire tension values. When a desired steering wire tension is achieved, the ECU 202 ceases actuation control signals 210 directed to the corresponding motor. Once minimum tensions have been established in each of the sheath steering wires the sheath 410 calibration is complete.

Catheter Attachment Module.

Figure 16:
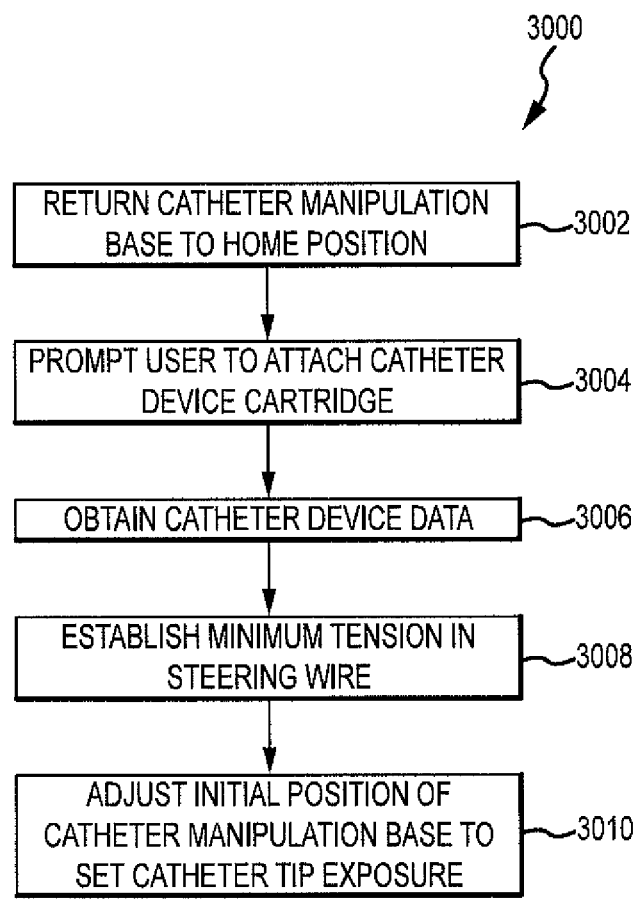
FIG. 16 is a flow chart illustrating an exemplary embodiment of a portion of the user-guided configuration routine logic directing the attachment of a catheter.

The illustrated embodiment of the user-guided configuration routine can contain a catheter attachment module 3000 depicted in FIG. 16. The catheter attachment module 3000 begins with step 3002, which comprises the ECU 202 generating a plurality of actuation control signals 210 and communicating them to the motor server 232 to return the manipulation base 308 to its home position, if it is not already positioned at the home position. While the user-guided configuration routine is repositioning the catheter manipulation base 308 to its home position, the configuration GUI 800 can display a status statement 806 and a status bar 802.

The illustrated embodiment of the catheter attachment module 3000 continues with step 3004. Step 3004 comprises the ECU 202 generating a status statement 806 prompting the user 224 to attach a catheter device cartridge 402 and waiting for confirmation that a catheter device cartridge 402 has been attached. Confirmation that a catheter device cartridge 402 has been attached can be accomplished by receipt of user input through a navigation button 808, illustrated in FIG. 12, or alternatively, by ECU 202 accessing an attachment signal generated by an attachment means of the manipulation base 308.

The illustrated embodiment of the catheter attachment module 3000 continues with step 3006. Step 3006 comprises the ECU 202 obtaining catheter device data, which can be accomplished in an embodiment by accessing the memory chip of the catheter device cartridge 402 to retrieve the encoded catheter data described above, such as, by way of example, the catheter physical dimensions. In such an embodiment, the memory chip is accessed through an electrical manipulator head and is transmitted to the ECU 202 through a signal or data transmission means such as a system bus or network. Where a catheter device cartridge 402 lacks a memory chip, or the manipulation base 308 lacks an electrical manipulator head, the ECU 202 can prompt the user 224 through a plurality of status statements 806 to input the catheter device data by way of one or more user input buttons 808. In an embodiment, the catheter device data can be stored in the computer readable storage media of the electronic control system 200 and can be accessed by the ECU 202.

While the catheter device data is being accessed, the status indicator icon 804 associated with the catheter is displayed as a working indicator, and when the catheter device data has been successfully acquired by the ECU 202, the ECU 202 can display a status statement 806 informing the user of successful attachment and display the status indicator icon 804 as a ready indicator within the configuration GUI 800.

The illustrated embodiment of the catheter attachment module 3000 continues with step 3008, which comprises establishing a minimum tension for each of the catheter steering wires to place the catheter 406 in a substantially undeflected orientation. The tensioning each steering wire to a minimum threshold can be accomplished by the ECU 202 by generating actuation control signals 210 directing movement of the fingers 316, 318, 320, 322 and by ECU 202 monitoring the motor state model 230 for changes in steering wire tension values. When a desired steering wire tension is achieved, the ECU 202 ceases actuation control signals 210 directed to the corresponding motor.

In an exemplary embodiment, the catheter attachment module 3000 concludes with step 3010. Step 3010 comprises the ECU 202 adjusting the initial position of the catheter manipulation base 308 to ensure the distal tip of the catheter 406 slightly protrudes from the sheath. The ECU 202 can determine the appropriate position for the manipulation base 308 by comparing the length of the catheter 406 and sheath 410, which are included within the catheter and sheath data discussed above, with the relative distance between the manipulation bases 308 and 310, available as part of the motor model state 230. The starting relative distance between the manipulation bases 308 and 310 should be substantially the same as the distance obtained by subtracting the sheath length from the catheter length. Adding this starting relative distance to the absolute position of the sheath manipulation base 310 yields a starting position for the catheter manipulation base 308. The ECU 202 can generate actuation control signals to the motor server 232 to move the catheter manipulation base 308 to the appropriate position. Although the above described embodiment includes the ECU 202 computing the position of the catheter manipulation base 308, those skilled in the art would appreciate that the position calculations could be made in other components of the system 10, such as, for example, the motion server 232.

In an alternative embodiment, the ECU 202 can include a configuration button 814 within the configuration GUI 800 allowing a user 224 to adjust the initial position of the distal end of the catheter 406, so as to increase, decrease, or eliminate its extension from the sheath 410. The ECU 202 can generate actuation control signals communicated to the motion server 232 to effect any position adjustments directed by the user 224 through the configuration GUI 800.

In an exemplary embodiment, the control logic 228 is configured to determine the necessary sequence of calibration steps based on the state of the RCGS 10 to achieve an indicated result. For example, the plurality of user-guided configuration routines displayed by the ECU 202 can include a "replace sheath" option that would, upon selection by the user 224, direct ECU 202 to determine the required calibration steps for a sheath replacement by executing the control logic 228. The diagnostic information maintained in the motor state model 230 and the device state model 234 allow the ECU 202 to determine if calibration steps directed to removal of a catheter 406 are necessary by determining if a catheter 406 is attached, such as, by way of example, reference to the attachment signal from the attachment means of the manipulation bases 308, 310. When attaching or replacing devices, the sheath 410, when used, must be calibrated before the catheter 406, and recalibration of a sheath 410 requires recalibration of an attached catheter 406 as well. Using these or similar logical constraints the control logic 228 can be configured to instruct the ECU 202 to select the appropriate calibration steps from those described above and greatly speed the calibration process by removing unnecessary steps.

In an exemplary embodiment, the plurality of user-guided configuration routines can include a startup routine, device attachment routine, a device replacement routine, a recovery routine, and a device breakage routine. As described above, the calibration steps of each routine can be determined by the ECU 202 by executing control logic 228.

The startup routine can include the ECU 202 prompting the user 224 to input the number and type of devices to be calibrated, as described above, while the device attachment and device replacement routines comprise attaching a new device, or detaching a device and attaching a replacement, respectively. The recovery routine can be used for recovering from an unexpected system error, such a loss of power or crash by the ECS 200. In such a routine the focus is not necessarily on replacing device, but rather on reestablishing the motor state model 230 and device state model 234 to determine if motor adjustments are required, such as adjusting steering wire tensions.

The device breakage routine can include a detection module for identifying malfunctioning devices in addition to the calibration steps previously described. For example, the ECU 202 can generate actuation control signals to instruct the motion server to effect a predetermined sequence of movements while the ECU 202 monitors the motor state model 230 and the device state model 234 to detect changes in data corresponding to the movement sequence. If corresponding data changes are not observed, the device is identified as malfunctioning and the ECU 202 can execute control logic 228 to identify the calibration steps necessary to replace it. In an alternative embodiment, the data values within the motor state model 230 and device state model 234 can have predetermined acceptable range values within the control logic 228, which when exceeded, can cause the ECU 202 to identify the associated device as malfunctioning.

It should be understood that the system 10, and particularly the ECU 202, as described above can include conventional processing apparatus known in the art, capable of executing pre-programmed instructions stored in an associated memory, all performing in accordance with the functionality described herein. It is contemplated that the methods and configuration routines described herein, including without limitation the configuration routine steps of embodiments of the invention, will be programmed in a preferred embodiment, with the resulting software being stored in an associated memory and where so described, can also constitute the means for performing such methods. Implementation of the invention, in software, in view of the foregoing enabling description, would require no more than routine application of programming skills by one of ordinary skill in the art. Such a system can further be of the type having both ROM, RAM, a combination of non-volatile and volatile (modifiable) memory so that the software can be stored and yet allow storage and processing of dynamically produced data and/or signals Although multiple embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the invention as defined in the appended claims.

What is claimed is:

1. A remotely based catheter guidance system, comprising:
a medical device manipulator assembly comprising at least one motor;
a medical device associated with the medical device manipulator assembly;
a display device; and
an electronic control unit (ECU) configured to control the display device and configured to send an actuation control signal to the at least one motor of the medical device manipulator assembly to control a plurality of actuation control units disposed within the medical device, wherein the actuation control signal is configured to move or bend the medical device, and wherein the ECU comprising a processor and a computer readable storage media containing logic, the ECU being configured to execute the logic to:
generate a user-guided configuration routine;
generate a configuration graphical user interface for providing information related to the user-guided configuration routine and receiving an input from a user;
display the configuration graphical user interface on the display; and
receive the input for configuring the medical device;
whereby the ECU calibrates the medical device in accordance with the input, and wherein the calibration by the ECU is configured to establish a minimum tension on at least one steering wire of the medical device.

2. The system of claim 1, the user-guided configuration routine including at least one of:
a device detachment module;
a catheter attachment module; and
a sheath attachment module.

3. The system of claim 2, the ECU being further configured to receive diagnostic data from at least one of the medical device manipulator assembly and the medical device.

4. The system of claim 3, the logic being configured to direct the ECU to include the at least one of the device detachment module, the catheter attachment module, and the sheath attachment module within the user-guided configuration routine in response the diagnostic data.

5. The system of claim 3, the ECU being further configured to execute the logic to identify coupled medical devices from the diagnostic data.

6. The system of claim 2, wherein the ECU executes at least one of the device detachment module, catheter attachment module, and sheath attachment module at the direction of the input.

7. The system of claim 2, the input indicating a configuration state and the ECU being configured to execute at least one of the device detachment module, catheter attachment module, and sheath attachment module to achieve the configuration state.

8. The system of claim 7, the ECU being further configured to receive diagnostic data from the remotely based catheter guidance system, the logic being configured to instruct the ECU to execute at least one of the device detachment module, catheter attachment module, and sheath attachment module using the diagnostic data to achieve the configuration state.

9. The system of claim 1, the input directing the configuration of at least one of:
a first medical device; and
the first medical device and a second medical device.

10. The system of claim 1, the configuration graphical user interface being further configured to include a status indicator for the medical device.

11. The system of claim 1, the configuration graphical user interface being further configured to display an indication that the remotely based catheter guidance system is performing an action in response to a received input.

12. The system of claim 1, wherein the configuration routine is executed by the ECU in response to at least one of:
startup of the remotely based catheter guidance system; and
receipt of user input directing the execution of the routine.

13. A method for configuring a medical device of a remotely based catheter guidance system, comprising:
displaying on a display device a configuration graphical user interface for conveying information and receiving user input directing the calibration of a medical device of a remotely based catheter guidance system;
receiving user input through the configuration graphical user interface directing the calibration of the medical device;
receiving data at an electronic control unit (ECU) from a medical device manipulator assembly;
analyzing the data to identify one or more configuration steps to be executed;
executing a configuration step in response to the user input comprising establishing a minimum tension on at least one steering wire of the medical device; and
sending actuation control signals from the ECU to at least one motor of the medical device manipulator assembly wherein the actuation control signals are configured to move or bend the medical device.

14. The method of claim 13, wherein the one or more configuration steps to be executed include at least one of:
a device detachment module;
a catheter attachment module; and
a sheath attachment module.

15. The method of claim 13, wherein the user input directs the configuration of at least one of:
a first medical device; and
the first medical device and a second medical device.

16. The method of claim 13, wherein the one or more configuration steps to be executed further comprise the steps of:
determining the system configuration;
returning any deflected medical devices to an undeflected state;
prompting the user to remove an attached catheter;
confirming that the attached catheter has been removed.

17. The method of claim 13, wherein the one or more configuration steps to be executed further comprise the steps of:
returning a manipulation base of the medical device manipulator assembly to a home position;
prompting the user to make translational position adjustments to the manipulation base;
prompting the user to attach a sheath device cartridge;
confirming the attachment of the sheath device cartridge;
obtaining sheath device data;
establishing a minimum tension for each sheath steering wire.

18. The method of claim 13, wherein the one or more configuration steps to be executed further comprise the steps of:
returning a manipulation base of the medical device manipulator assembly to a home position;
prompting the user to attach a catheter device cartridge;

confirming the attachment of the catheter device cartridge;
obtaining catheter device data;
establishing a minimum tension for each catheter steering wire.

* * * * *